United States Patent [19]
Mitchinson et al.

[11] Patent Number: 5,736,499
[45] Date of Patent: Apr. 7, 1998

[54] MUTANT A-AMYLASE

[75] Inventors: Colin Mitchinson, Half Moon Bay; Carol Ann Requadt, Tiburon; Traci Helen Ropp, San Francisco, all of Calif.; Leif P. Solheim, Clinton, Iowa

[73] Assignee: Genencor International, Inc., Rochester, N.Y.

[21] Appl. No.: 468,700

[22] Filed: Jun. 6, 1995

[51] Int. Cl.$^6$ .................................................. C11D 3/386
[52] U.S. Cl. .................... 510/392; 510/393; 510/530; 435/201; 435/202; 435/203; 435/204
[58] Field of Search .................. 252/174.12, DIG. 12; 435/201, 202, 203, 204; 510/392, 393, 530

[56] References Cited

U.S. PATENT DOCUMENTS 5,364,782  11/1994  Quax et al. ................. 435/202

FOREIGN PATENT DOCUMENTS

| | | |
|---|---|---|
| 2676456 | 5/1991 | France . |
| 9100353 | 1/1991 | WIPO . |
| 9402597 | 3/1994 | WIPO . |
| 9418314 | 8/1994 | WIPO . |

*Primary Examiner*—Paul Lieberman
*Assistant Examiner*—Kery A. Fries
*Attorney, Agent, or Firm*—Christopher L. Stone

[57] ABSTRACT

Novel α-amylase enzymes are disclosed in which one or more asparagine residues are substituted with a different amino acid or deleted. The disclosed α-amylase enzymes show altered or improved low pH starch hydrolysis performance, stability and activity profiles.

25 Claims, 17 Drawing Sheets

```
                                      188
N188T 5'-G GAT TGG GAA GTG TCG ACT GAA AAC GGC AAC TAT GAT-3' (SEQ ID NO:4)
                              SalI

N188P 5'-G GAT TGG GAA GTT TCC CCA GAA AAT GGC AAC TAT GAT-3' (SEQ ID NO:5)
                                   pflMI N188R 5'-G GAT TGG GAA GTT TCT AGA GAA AAC GGC AAC TAT GAT-3' (SEQ ID NO:6)
                                   XbaI N188L 5'-G GAT TGG GAA GTT TCC CTC GAG AAC GGC AAC TAT GAT-3' (SEQ ID NO:7)
                                   XhoI N188A 5'-G GAT TGG GAA GTT TCG GCC GAA AAC GGC AAC TAT GAT-3' (SEQ ID NO:8)
                                   EagI N188G 5'-G GAT TGG GAA GTT TCC GGA GAA AAC GGC AAC TAT GAT-3' (SEQ ID NO:9)
                                   BspEI N188V 5'-G GAT TGG GAA GTT AGC GTC GAA AAC GGC AAC TAT GAT-3' (SEQ ID NO:10)
                                   HgaI N188K 5'-G GAT TGG GAA GTT TCC AAG GAA AAC GGC AAC TAT GAT-3' (SEQ ID NO:11)
                                   StyI N188Q 5'-G GAT TGG GAA GTT TCC CAG GAA AAT GGC AAC TAT GAT-3' (SEQ ID NO:12)
                                   BstXI N188H 5'-G GAT TGG GAA GTT TCT CAT GAA AAC GGC AAC TAT GAT-3' (SEQ ID NO:13)
                                   BspHI
```

| | | | | | | | | |
|---|---|---|---|---|---|---|---|---|
| N188T | 5'-G GAT TGG GAA GTG TCG | ACT | GAA AAC GGC AAC TAT GAT-3' | (SEQ ID NO:4) |
| | | Sal I | | |
| N188P | 5'-G GAT TGG GAA GTT TCC | CCA | GAA AAT GGC AAC TAT GAT-3' | (SEQ ID NO:5) |
| | | | pflMI | |
| N188R | 5'-G GAT TGG GAA GTT TCT | AGA | GAA AAC GGC AAC TAT GAT-3' | (SEQ ID NO:6) |
| | | Xba I | | |
| N188L | 5'-G GAT TGG GAA GTT TCC | CTC | GAG AAC GGC AAC TAT GAT-3' | (SEQ ID NO:7) |
| | | Xho I | | |
| N188A | 5'-G GAT TGG GAA GTT TCG | GCC | GAA AAC GGC AAC TAT GAT-3' | (SEQ ID NO:8) |
| | | Eag I | | |
| N188G | 5'-G GAT TGG GAA GTT TCC | GGA | GAA AAC GGC AAC TAT GAT-3' | (SEQ ID NO:9) |
| | | BspE I | | |
| N188V | 5'-G GAT TGG GAA GTT AGC | GTC | GAA AAC GGC AAC TAT GAT-3' | (SEQ ID NO:10) |
| | | Hga I | | |
| N188K | 5'-G GAT TGG GAA GTT TCC | AAG | GAA AAT GGC AAC TAT GAT-3' | (SEQ ID NO:11) |
| | | Sty I | | |
| N188Q | 5'-G GAT TGG GAA GTT TCC | CAG | GAA AAC GGC AAC TAT GAT-3' | (SEQ ID NO:12) |
| | | BstX I | | |
| N188H | 5'-G GAT TGG GAA GTT TCT | CAT | GAA AAC GGC AAC TAT GAT-3' | (SEQ ID NO:13) |
| | | BspH I | | |

FIG._1A

```
N188E  5'-G GAT TGG GAA GTT TCC GAA GAG AAC GGC AAC TAT GAT-3'  (SEQ ID NO:14)
                                        Earl
N188D  5'-G GAT TGG GAA GTT TCC GAG GAG AAC GGC AAC TAT GAT-3'  (SEQ ID NO:15)
                                            BseRI
N188Y  5'-G GAT TGG GAA GTT TCA TAT GAA AAC GGC AAC TAT GAT-3'  (SEQ ID NO:16)
                                        NdeI
N188C  5'-G GAT TGG GAA GTC TCC TGC GAA AAC GGC AAC TAT GAT-3'  (SEQ ID NO:17)
                               BsmAI
N188F  5'-G GAT TGG GAA GTT TCC TTC GAA AAC GGC AAC TAT GAT-3'  (SEQ ID NO:18)
                                            BstBI
N188I  5'-G GAT TGG GAA GTT TCG ATC GAA AAC GGC AAC TAT GAT-3'  (SEQ ID NO:19)
                                    PvuI
N188M  5'-G GAT TGG GAA GTT TCC ATG GAA AAC GGC AAC TAT GAT-3'  (SEQ ID NO:20)
N188W  5'-G GAT TGG GAA GTT TCC TGG GAA AAC GGC AAC TAT GAT-3'  (SEQ ID NO:21)
                                        BstNI
N188S  5'-G GAT TGG GAA GTG AGC TCT GAA AAC GGC AAC TAT GAT-3'  (SEQ ID NO:22)
                                    SstI
```

FIG._1B

| | | |
|---|---|---|
| PCR A+ | 5'-AGG AAA GGC TTG GGA TTG GGA AGT-3' | (SEQ ID NO:23) |
| PCR A− | 5'-ACT TCC CAA TCC CAA GCC TTT CCT-3' | (SEQ ID NO:24) |
| PCR B+ | 5'-GGC AAC TAT GAT TAT TTG ATG TAT-3' | (SEQ ID NO:25) |
| PCR B− | 5'-ATA CAT CAA ATA ATC ATA GTT GCC-3' | (SEQ ID NO:26) |
| PCR LAAfs5 | 5'-CTT CAT TCC CGC GAC ATT AAC-3' | (SEQ ID NO:27) |
| PCR ClaI-SalI | 5'-GA TTC CCT TGT GAG AAT AAA AG-3' | (SEQ ID NO:28) |
| PCR I+ | 5'-AAT CAT GTC AGG GAA AAA ACT GGG-3' (BsrI) | (SEQ ID NO:29) |
| PCR I− | 5'-CCC AGT TTT TTC CCT GAC ATG ATT-3' (BsrI) | (SEQ ID NO:30) |
| PCR J+ | 5'-TTT ACG GTA GCT GAA TAT TGG CAG-3' | (SEQ ID NO:31) |
| PCR J− | 5'-CTG CCA ATA TTC AGC TAC CGT AAA-3' | (SEQ ID NO:32) |

Position numbers appear above the 5' ends: 179, 179, 191, 191, 90, 356, 246, 246, 257, 257.

FIG._2

```
AGCTTGAAGA AGTGAAGAAG CAGAGAGGCT ATTGAATAAA TGAGTAGAAA GCGCCATATC    60

GGCGCTTTTC TTTTGGAAGA AAATATAGGG AAAATGGTAC TTGTTAAAAA TTCGGAATAT   120

TTATACAACA TCATATGTTT CACATTGAAA GGGGAGGAGA ATCATGAAAC AACAAAAACG   180
                                                M  K  Q  Q  K  R

GCTTTACGCC CGATTGCTGA CGCTGTTATT TGCGCTCATC TTCTTGCTGC CTCATTCTGC   240
 L  Y  A   R  L  L  T   A  L  L  F   A  L  I   F  L  L  P   H  S  A

AGCAGCGGCG GCAAATCTTA ATGGGACGCT GATGCAGTAT TTTGAATGGT ACATGCCCAA   300
  A  A  A   A  N  L  N   G  T  L   M  Q  Y   F  E  W  Y   M  P  N

TGACGGCCAA CATTGGAAGC GTTTGCAAAA CGACTCGGCA TATTTGGCTG AACACGGTAT   360
 D  G  Q   H  W  K  R   L  Q  N   D  S  A   Y  L  A  E   H  G  I

TACTGCCGTC TGGATTCCCC CGGCATATAA GGGAACGAGC CAAGCGGATG TGGGCTACGG   420
 T  A  V   W  I  P  P   A  Y  K   G  T  S   Q  A  D  V   G  Y  G

TGCTTACGAC CTTTATGATT TAGGGGAGTT TCATCAAAAA GGGACGGTTC GGACAAAGTA   480
 A  Y  D   L  Y  D  L   G  E  F   H  Q  K   G  T  V  R   T  K  Y

CGGCACAAAA GGAGAGCTGC AATCTGCGAT CAAAAGTCTT CATTCCCGCG ACATTAACGT   540
 G  T  K   G  E  L  Q   S  A  I   K  S  L   H  S  R  D   I  N  V

TTACGGGGAT GTGGTCATCA ACCACAAAGG CGGCGCTGAT GCGACCGAAG ATGTAACCGC   600
 Y  G  D   V  V  I  N   H  K  G   G  A  D   A  T  E  D   V  T  A

GGTTGAAGTC GATCCCGCTG ACCGCAACCG CGTAATTTCA GGAGAACACC TAATTAAAGC   660
 V  E  V   D  P  A  D   R  N  R   V  I  S   G  E  H  L   I  K  A
```

```
CTGGACACAT TTTCATTTTC CGGGGCGCGG CAGCACATAC AGCGATTTTA AATGGCATTG    720
 W  T  H    F  H  F  P    G  R  G    S  T  Y    S  D  F  K    W  H  W

GTACCATTTT GACGGAACCG ATTGGGACGA GTCCCGAAAG CTGAACCGCA TCTATAAGTT    780
 Y  H  F    D  G  T  D    W  D  E    S  R  K    L  N  R  I    Y  K  F

TCAAGGAAAG GCTTGGGATT GGGAAGTTTC CAATGAAAAC GGCAACTATG ATTATTTGAT    840
 Q  G  K    A  W  D  W    E  V  S    N  E  N    G  N  Y  D    Y  L  M

GTATGCCGAC ATCGATTATG ACCATCCTGA TGTCGCAGCA GAAATTAAGA GATGGGGCAC    900
 Y  A  D    I  D  Y  D    H  P  D    V  A  A    E  I  K  R    W  G  T

TTGGTATGCC AATGAACTGC AATTGGACGG TTTCCGTCTT GATGCTGTCA AACACATTAA    960
 W  Y  A    N  E  L  Q    L  D  G    F  R  L    D  A  V  K    H  I  K

ATTTTCTTTT TTGCGGGATT GGGTTAATCA TGTCAGGGAA AAAACGGGGA AGGAAATGTT   1020
 F  S  F    L  R  D  W    V  N  H    V  R  E    K  T  G  K    E  M  F

TACGGTAGCT GAATATTGGC AGAATGACCT TGATGTGCCT CTGCATTATC AGTTCCATGG   1080
 T  V  A    E  Y  W  Q    N  D  L    D  V  P    L  H  Y  Q    F  H  G

AAATTTCAAT CATTCAGTTT TCGATGTTCC TAGAAAACTT AACGGAACTG TTGTTTCAAA   1140
 N  F  N    H  S  V  F    D  V  P    R  K  L    N  G  T  V    V  S  K

ACAGGGAGGC GGCTATGATA TGAGGAAACT GAACGGGACG GTCGTTTCCA AACATCCAAC   1200
 Q  G  G    G  Y  D  M    R  K  L    N  G  T    V  V  S  K    H  P  T

GTTGAAATCG GTTACATTTG TCGATAACCA TGATACACAG CCGGGGCAAT CGCTTGAGTC   1260
 L  K  S    V  T  F  V    D  N  H    D  T  Q    P  G  Q  S    L  E  S

GACTGTCCAA ACATGGTTTA AGCCGCTTGC TTACGCTTTT ATTCTCACAA GGGAATCTGG   1320
 T  V  Q    T  W  F  K    P  L  A    Y  A  F    I  L  T  R    E  S  G
```

```
ATACCCTCAG GTTTTCTACG GGGATATGTA CGGGACGAAA GGAGACTCCC AGCGCGAAAT    1380
    Y  P  Q   V  F  Y  G   D  M  Y    G  T  K    G  D  S  Q   R  E  I

TCCTGCCTTG AAACACAAAA TTGAACCGAT CTTAAAGCG AGAAAACAGT ATGCGTACGG    1440
    P  A  L   K  H  K  I   E  P  I    L  K  A    R  K  Q  Y   A  Y  G

AGCACAGCAT GATTATTTCG ACCACCATGA CATTGTCGGC TGGACAAGGG AAGGCGACAG    1500
    A  Q  H   D  Y  F  D   H  H  D    I  V  G    W  T  R  E   G  D  S

CTCGGTTGCA AATTCAGGTT TGGCGGCATT AATAACAGAC GGACCCGGTG GGGCAAAGCG    1560
    S  V  A   N  S  G  L   A  A  L    I  T  D    G  P  G  G   A  K  R

AATGTATGTC GGCCGGCAAA ACGCCGGTGA GACATGGCAT GACATTACCG GAAACCGTTC    1620
    M  Y  V   G  R  Q  N   A  G  E    T  W  H    D  I  T  G   N  R  S

GGAGCCGGTT GTCATCAATT CGGAAGGCTG GGGAGAGTTT CACGTAAACG GCGGGTCGGT    1680
    E  P  V   V  I  N  S   E  G  W    G  E  F    H  V  N  G   G  S  V

TTCAATTTAT GTTCAAAGAT AGAAGAGCAG AGAGGACGGA TTTCCTGAAG GAAATCCGTT    1740
    S  I  Y   V  Q  R  *

TTTTTATTTT GCCCGTCTTA TAAATTTCTT TGATTACATT TTATAATTAA TTTTAACAAA    1800

GTGTCATCAG CCCTCAGGAA GGACTTGCTG ACAGTTTGAA TCGCATAGGT AAGGCGGGGA    1860

TGAAATGGCA ACGTTATCTG ATGTAGCAAA GAAAGCAAAT GTGTCGAAAA TGACGGTATC    1920

GCGGGTGATC AATCATCCTG AGACTGTGAC GGATGAATTG AAAAAGCT              1968
```

FIG._3C

```
ANLNGTLMQY  FEWYMPNDGQ  HWKRLQNDSA  YLAEHGITAV  WIPPAYKGTS  QADVGYGAYD   60

LYDLGEFHQK  GTVRTKYGTK  GELQSAIKSL  HSRDINVYGD  VVINHKGAD   ATEDVTAVEV  120

DPADRNRVIS  GEHLIKAWTH  FHFPGRGSTY  SDFKWHWYHF  DGTDWDESRK  LNRIYKFQGK  180

AWDWEVSNEN  GNYDYLMYAD  IDYDHPDVAA  EIKRWGTWYA  NELQLDGFRL  DAVKHIKFSF  240

LRDWNHVRE   KTGKEMFTVA  EYWQNDLGAL  ENYLNKTNFN  HSVFDVPLHY  QFHAASTQGG  300

GYDMRKLLNG  TVVSKHPLKS  VIFVDNHDTQ  PGQSLESTVQ  TWFKPLAYAF  ILTRESGYPQ  360

VFYGDMYGTK  GDSQREIPAL  KHKIEPILKA  RKQYAYGAQH  DYFDHHDIVG  WTREGDSSVA  420

NSGLAALITD  GPGGAKRMYV  GRQNAGETWH  DITGNRSEPV  VINSEGWGEF  HVNGGSVSIY  480

VQR
```

*FIG._4*

```
Am-Lich  = B.llcheniformis    Am-Amylo = B.amyloliquefaciens    Am-Stero = B.stearothermophilus.

1       19
                                                                                             1
Am-Lich      .....MKQQ  KRLYARLLTL  LFALIFLLPH  ......SAAA  AANLNGTLMQ  YFEWYMPNDG
Am-Amylo     MRGRGNMIQK  RKRTVSFRLV  LMCTLLFVSL  ......PITK  TSAVNGTLMQ  YFEWYTPNDG
Am-Stearo    ......VLTF  HRIIRKGWMF  LLAFLLTASL  FCPTGRHAKA  AAPFNGTMMQ  YFEWYLPDDG 61                                                                      79
                                                                                     120
Am-Lich      QHWKRLQNDS  AYLAEHGITA  VWIPPAYKGT  SQADVGYGAY  DLYDLGEFHQ  KGTVRTKYGT
Am-Amylo     QHWKRLQNDA  EHLSDIGITA  VWIPPAYKGL  SQSDNGYGPY  DLYDLGEFQQ  KGTVRTKYGT
Am-Stearo    TLWTKVANEA  NNLSSLGITA  LSLPPAYKGT  SRSDVGYGVY  DLYDLGEFNQ  KGTVRTKYGT 121                                                                     139
                                                                                     180
Am-Lich      KGELQSAIKS  LHSRDINVYG  DVVINHKGGA  DATEDVTAVE  VDPADRNRVI  SGEHLIKAWT
Am-Amylo     KSELQDAIGS  LHSRNVQVYG  DVVLNHKAGA  DATEDVTAVE  VNPANRNQET  SEEYQIKAWT
Am-Stearo    KAQYLQAIQA  AHAAGMQVYA  DVVFDHKGGA  DGTEWVDAVE  VNPSDRNQEI  SGTYQIQAWT 181                                                                     197
                                                                                     240
Am-Lich      HFHFPGRGST  YSDFKWHWYH  FDGTDWDESR  KLNRIYKF..  QGKAWDWEVS  NENGNYDYLM
Am-Amylo     DFRFPGRGNT  YSDFKWHWYH  FDGADWDESR  KISRIFKFRG  EGKAWDWEVS  SENGNYDYLM
Am-Stearo    KFDFPGRGNT  YSSFKWRWYH  FDGVDWDESR  KLSRIYKFRG  IGKAWDWEVD  TENGNYDYLM 241                                                                     257
                                                                                     300
Am-Lich      YADIDYDHPD  VAAEIKRWGT  WYANELQLDG  FRLDAVKHIK  FSFLRDWVNH  VREKTGKEMF
Am-Amylo     YADVDYDHPD  VVAETKKWGI  WYANELSLDG  FRIDAAKHIK  FSFLRDWVQA  VRQATGKEMF
Am-Stearo    YADLDMDHPE  VVTELKNWGK  WYVNTTNIDG  FRLDGLKHIK  FSFFPDWLSY  VRSQTGKPLF
```

FIG._5A

Am-Lich = B.llcheniformis   Am-Amylo = B.amyloliquefaciens   Am-Stero = B.stearothermophilus.

```
          301
Am-Lich   TVAEYWQNDL GALENYLNKT NFNHSVFDVP LHYQFHAAST QGGGYDMRKL LNGTVVSKHP  317
Am-Amylo  TVAEYWQNNA GKLENYLNKT SFNQSVFDVP LHFNLQAASS QGGGYDMRRL LDGTVVSRHP  360
Am-Stearo TVGEYWSYDI NKLHNYITKT NGTMSLFDAP LHNKFYTASK SGGAFDMRTL MTNTLMKDQP 361
Am-Lich   LKSVTFVDNH DTQPGQSLES TVQTWFKPLA YAFILTRESG YPQVFYGDMY GTKGDSQREI  377
Am-Amylo  EKAVTFVENH DTQPGQSLES TVQTWFKPLA YAFILTRESG YPQVFYGDMY GTKGTSPKEI  420
Am-Stearo TLAVTFVDNH DTNPAKR.CS HGRPWFKPLA YAFILTRQEG YPCVFYGDYY GI...PQYNI 421
Am-Lich   PALKHKIEPI LKARKQYAYG AQHDYFDHHD IVGWTREGDS SVANSGLAAL ITDGPGGAKR  437
Am-Amylo  PSLKDNIEPI LKARKEYAYG PQHDYIDHPD VIGWTREGDS SAAKSGLAAL ITDGPGGSKR  480
Am-Stearo PSLKSKIDPL LIARRDYAYG TQHDYLDHSD IIGWTREGVT EKPGSGLAAL ITDGAGRSKW 481                                     483
Am-Lich   MYVGRQNAGE TWHDITGNRS EPVVINSEGW GEFHVNGGSV SIYVQR.....             540
Am-Amylo  MYAGLKNAGE TWYDITGNRS DTVKIGSDGW GEFHVNDGSV SIYVQK.....             ......
Am-Stearo MYVGKQHAGK VFYDLTGNRS DTVTINSDGW GEFKVNGGSV SVWVPRKTTV STIARPITTR 541                   559
Am-Lich   ..........  ..........
Am-Amylo  ..........  ..........
Am-Stearo PWTGEFVRWH  EPRLVAWP*
```

FIG._5B

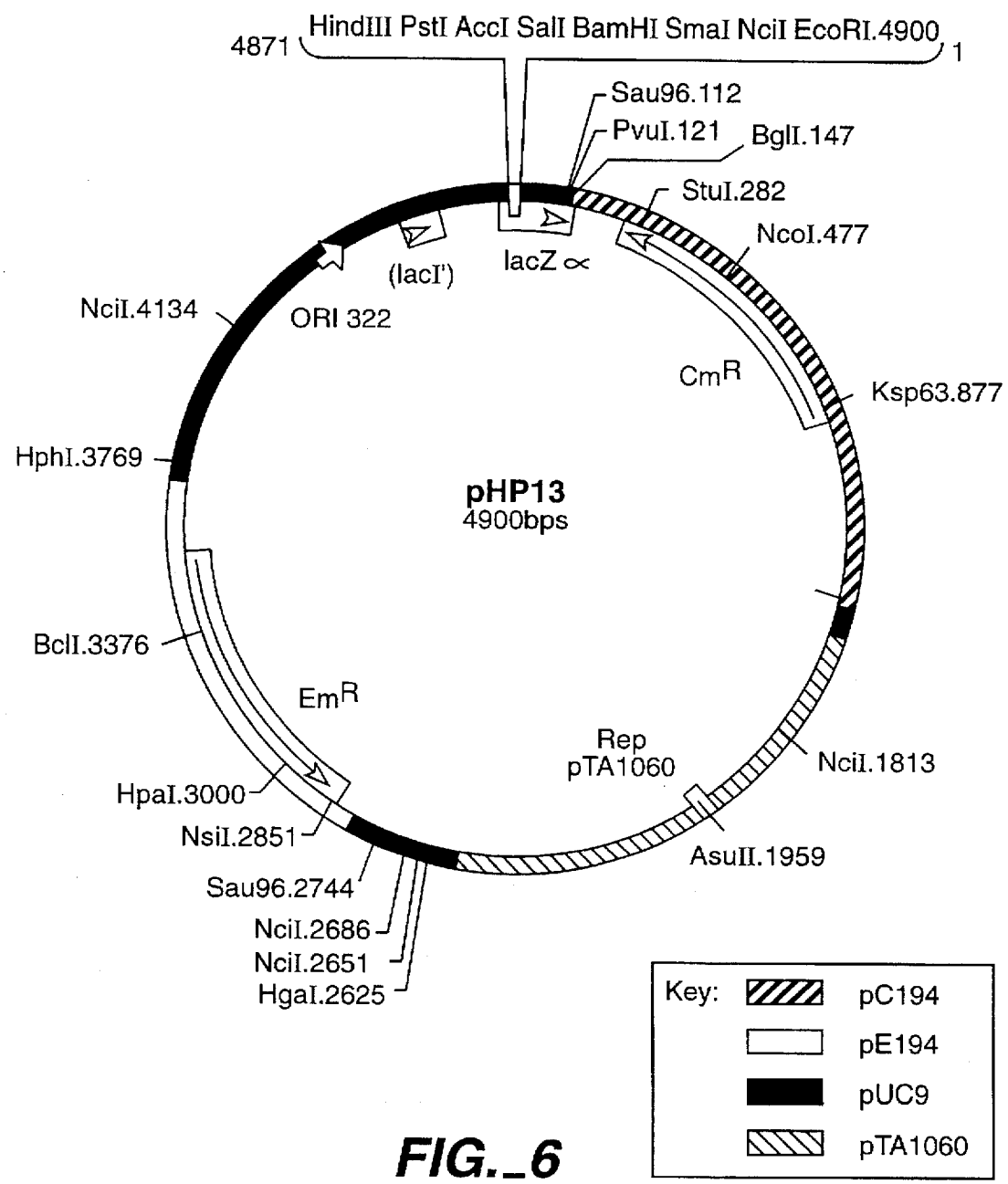
FIG._6

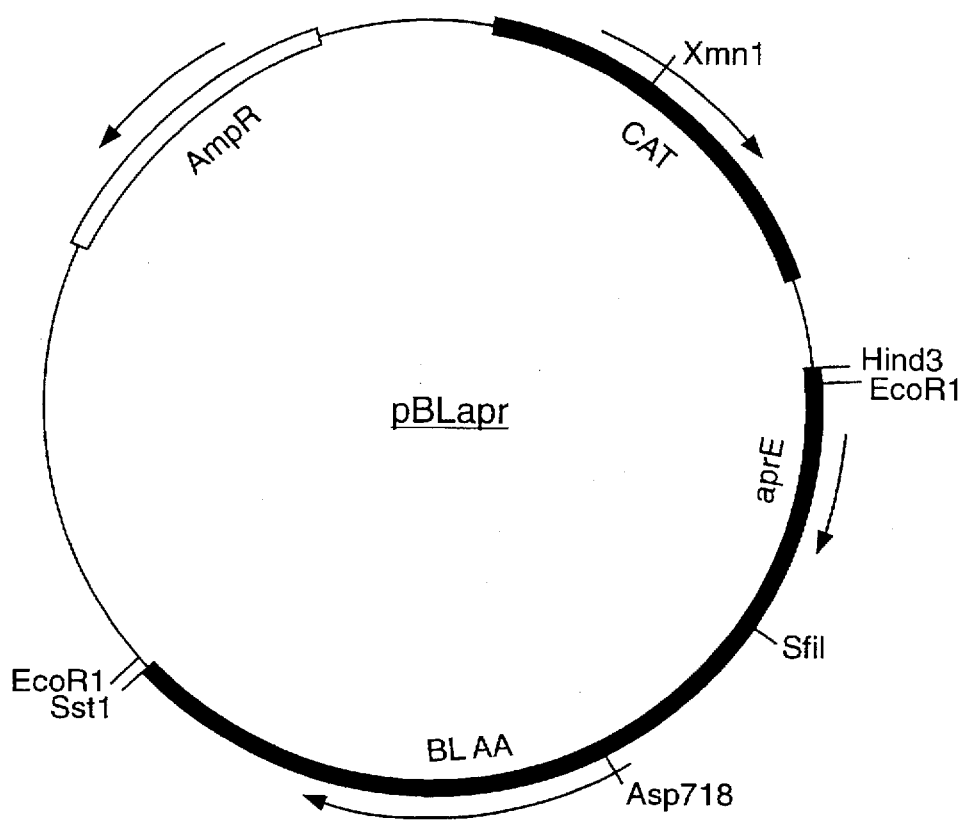
FIG._7

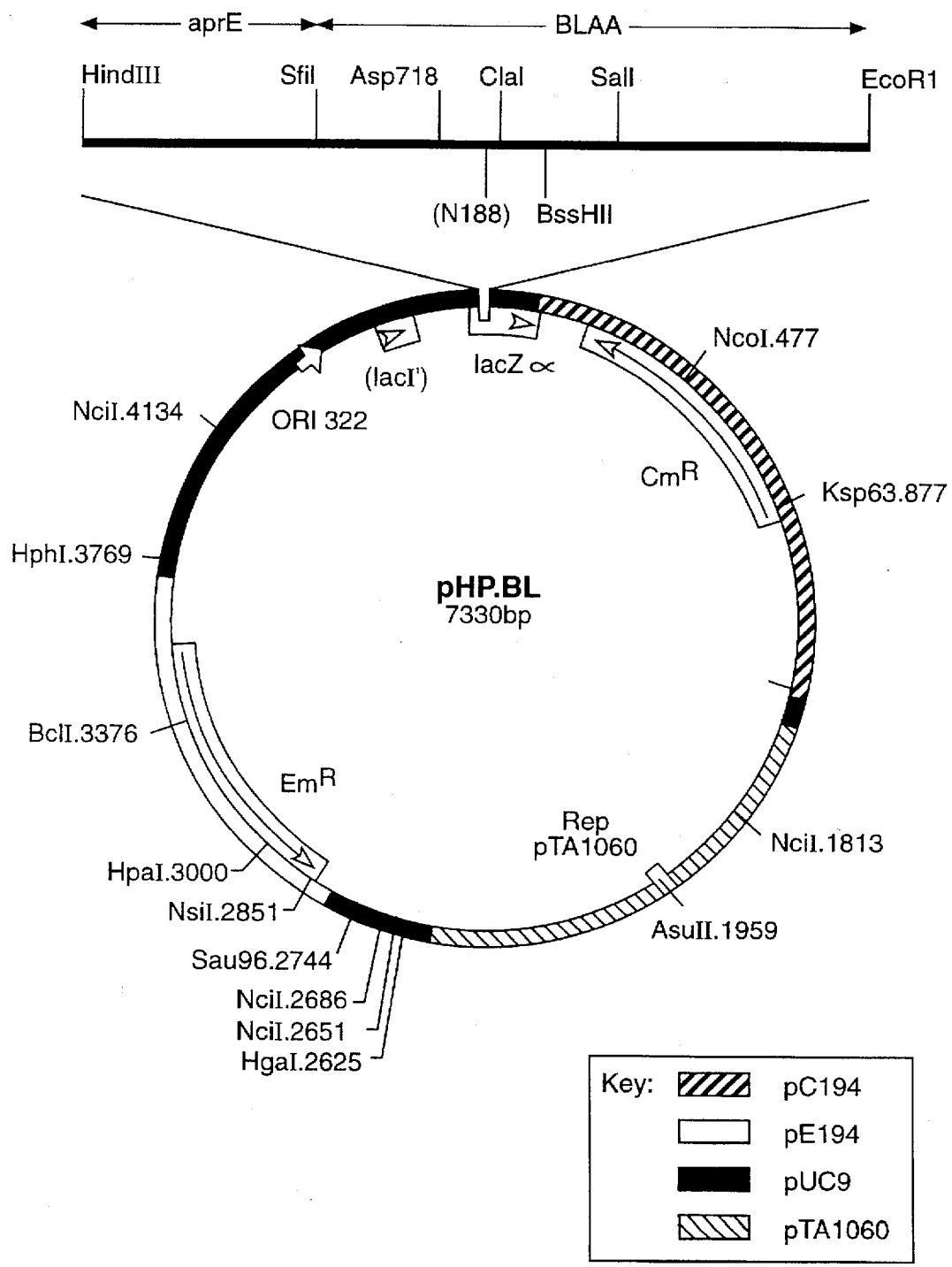
FIG._8

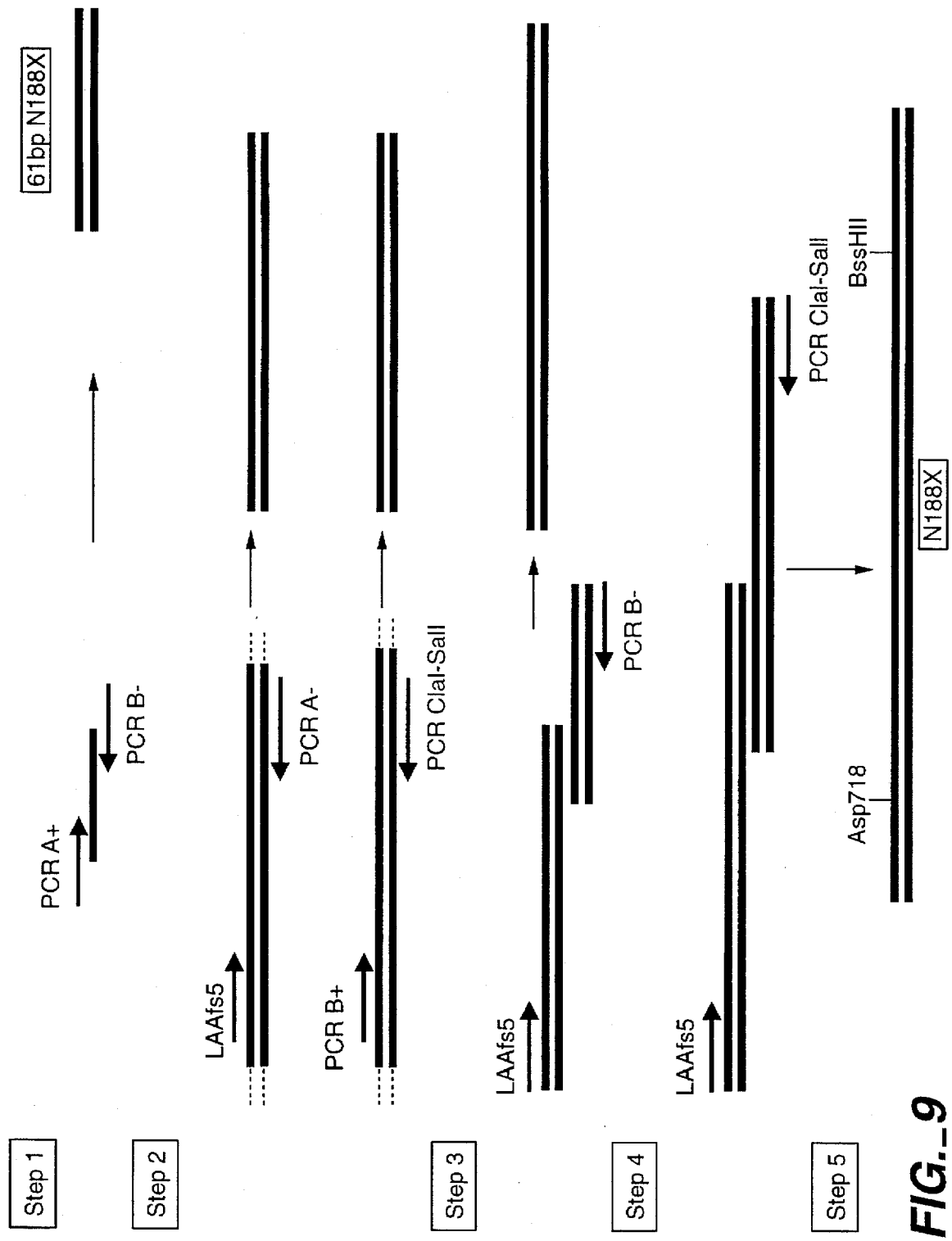
FIG._9

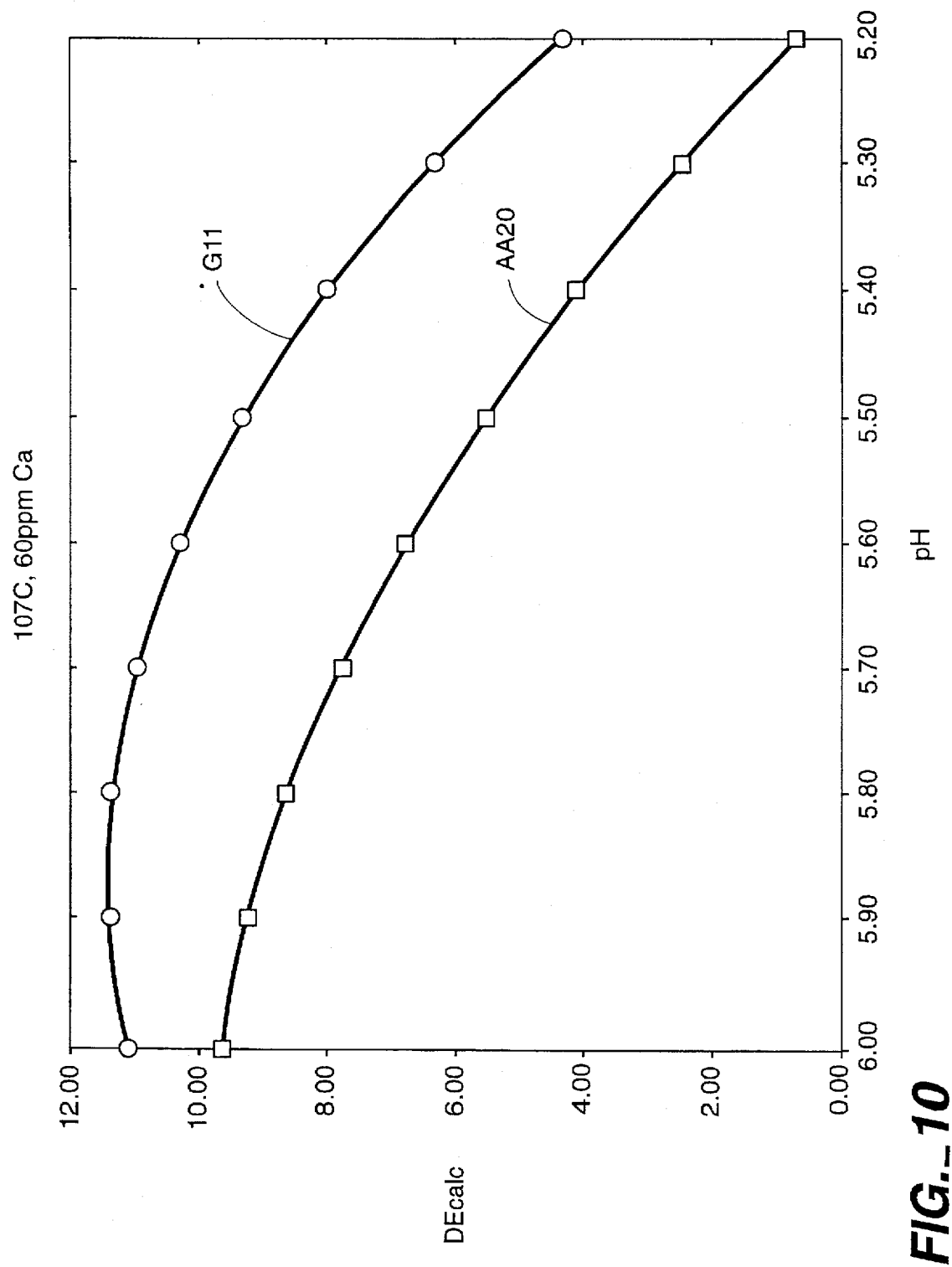
FIG._10

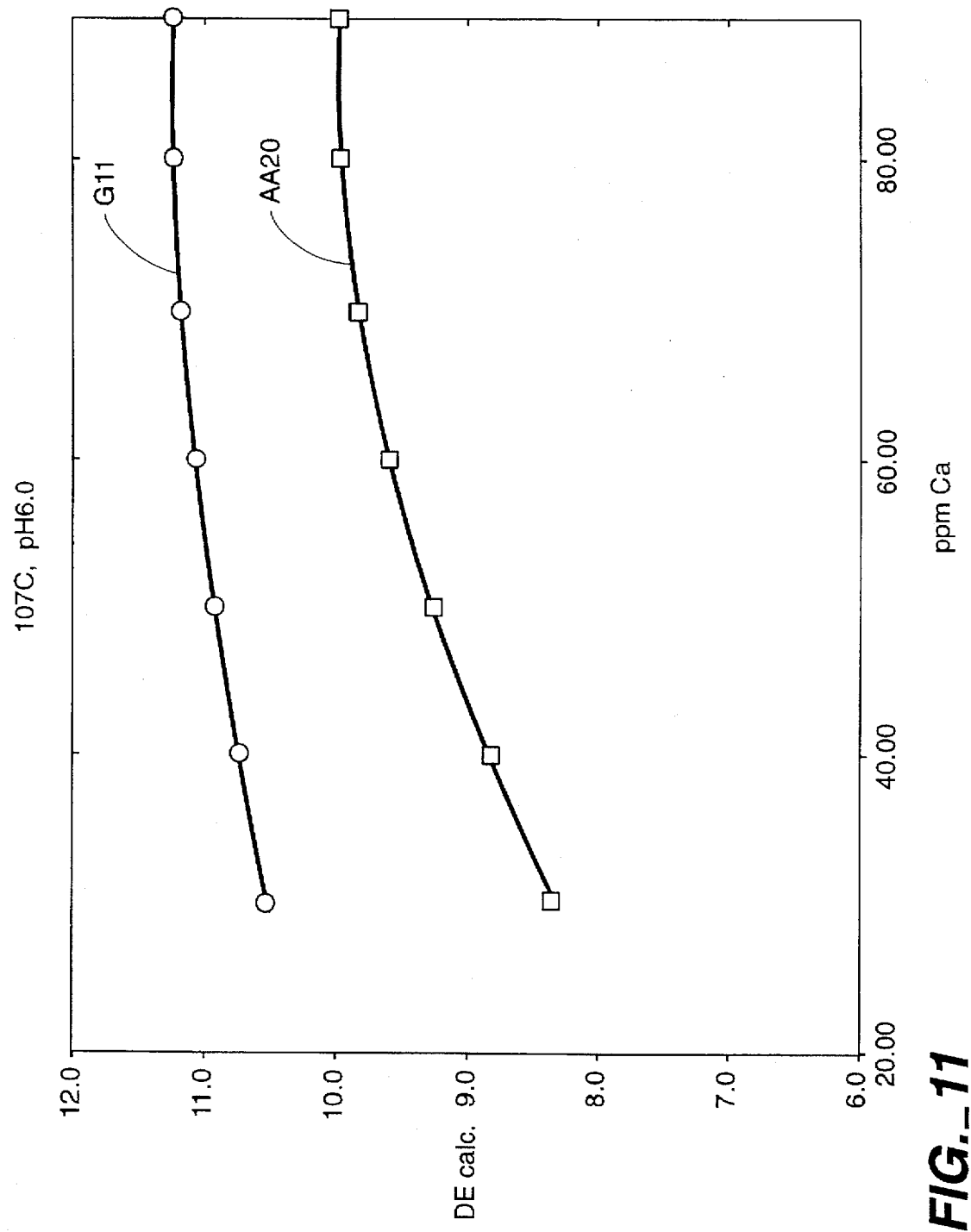
FIG._11

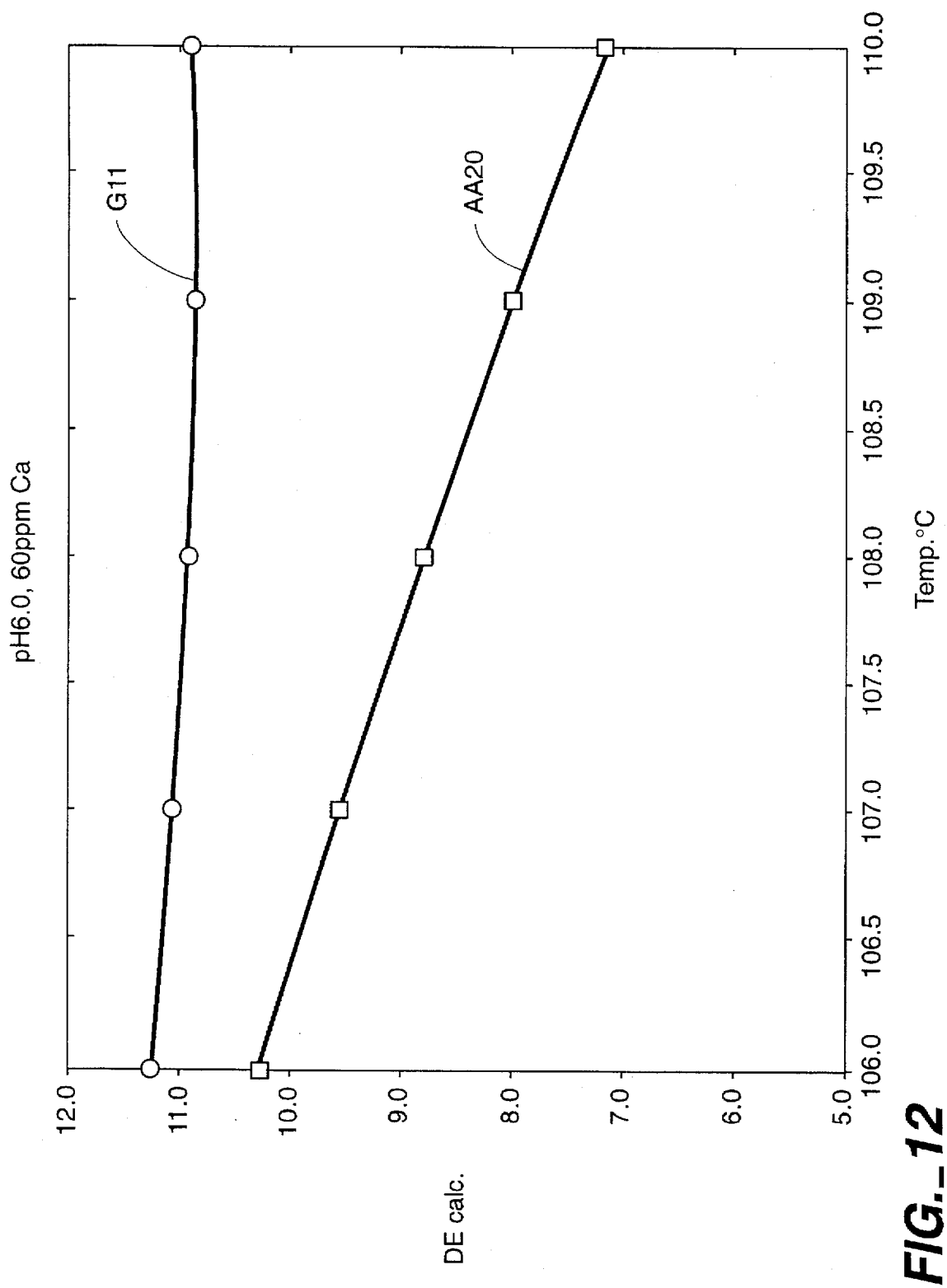
FIG._12

SIGNAL SEQUENCE-MATURE PROTEIN JUNCTIONS IN:

*B.licheniformis*  alpha-amylase.

M K Q Q K R L T A R L L T L L F A L I F L L L P H S A A A A A N L . . . . . . . . . .
⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀(PstI)↓

*B.subtilis*  alkaline protease aprE.

M R S K T L W I S L L F A L T L I F T M A F S N M S A Q A A A G K S . . . . . . . . . .
⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀⠀(PstI)↓

*B.licheniformis*  alpha-amylase in pBLapr.

M R S K T L W I S L L F A L T L I F T M A F S N M S A Q A A A N L . . . . . . . . . .

(PstI)   indicates the site of the restriction site in the gene

BOLD TYPE indicates the N-terminus of the secreted protein in *Bacillus*.

*FIG._13*

MUTANT α-AMYLASE

FIELD OF THE INVENTION

The present invention is directed to α-amylases having altered performance characteristics. Particularly, the present invention is directed to novel mutant α-amylase enzymes having an asparagine residue which is substituted with a different amino acid or deleted, wherein the resultant α-amylase exhibits altered low pH starch hydrolysis performance, altered stability and altered activity profiles.

BACKGROUND OF THE INVENTION

α-Amylases (α-1,4-glucan-4-glucanohydrolase, EC 3.2.1.1) hydrolyze internal α1,4-glucosidic linkages in starch, largely at random, to produce smaller molecular weight malto-dextrins. α-Amylases are of considerable commercial value, being used in the initial stages (liquefaction) of starch processing; in alcohol production; as cleaning agents in detergent matrices; and in the textile industry for starch desizing. α-Amylases are produced by a wide variety of microorganisms including Bacillus and Aspergillus, with most commercial amylases being produced from bacterial sources such as *Bacillus licheniformis*, *Bacillus amyloliquefaciens*, *Bacillus subtills*, or *Bacillus stearothermophilus*. In recent years, the preferred enzymes in commercial use have been those from *Bacillus licheniformis* because of their heat stability and performance, at least at neutral and mildly alkaline pH's.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from *Bacillus licheniformis*, with the addition of calcium hydroxide, sodium hydroxide or sodium carbonate. The addition of calcium hydroxide has the advantage of also providing calcium ions which are known to stabilize the α-amylases against inactivation. Upon addition of α-amylases, the suspension is pumped through a steam jet to instantaneously raise the temperature to between 80°–115° C. The starch is immediately gelatinized and, due to the presence of α-amylases, depolymerized through random hydrolysis of α(1–4) glycosidic bonds to a fluid mass which is easily pumped.

In a second variation to the liquefaction process, α-amylase is added to the starch suspension, the suspension is held at a temperature of 80°–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was obtained and the molecular structure of the α-amylase molecule. α-Amylases produced by wild type strains of *Bacillus subtilis* or *Bacillus amyloliquefacians* are typically used at temperatures no greater than about 90° C. due to excessively rapid thermal inactivation above that temperature, whereas α-amylases produced by wild type strains of *Bacillus licheniformis* can be used at temperatures up to about 110° C. The presence of starch and calcium ion are known to stabilize α-amylases against inactivation. Nonetheless, α-amylases are used at pH values above 6 to protect against rapid inactivation. At low temperatures, α-amylase from *Bacillus licheniformis* is known to display hydrolyzing activity on starch substrate at pH values as low as 5. However, when the enzyme is used for starch hydrolysis at common jet temperatures, e.g., between 102° C. and 109° C., the pH must be maintained above at least pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH is generally maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose with glucoamylase, requires a pH of 4–4.5; therefore, the pH must be adjusted down from 5.9–6.0 to 4–4.5; requiring additional chemical addition and refining steps.

Subsequent to liquefaction, the processed starch is saccharified to glucose with glucoamylase. A problem with present processes occurs when residual starch is present in the saccharification mixture due to an incomplete liquefaction of the starch, e.g., inefficient amylose hydrolysis by amylase. Residual starch is highly resistant to glucoamylase hydrolysis. It represents a yield loss and interferes with downstream filtration of the syrups.

Additionally, many α-amylases are known to require the addition of calcium ion for stability. This further increases the cost of liquefaction.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or α-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 94/02597, a mutant α-amylase having improved oxidative stability is described wherein one or more methionines are replaced by any amino acid except cysteine or methionine.

In PCT publication No. WO 94/18314, a mutant α-amylase having improved oxidative stability is described wherein one or more of the methionine, tryptophan, cysteine, histidine or tyrosine residues is replaced with a non-oxidizable amino acid.

In PCT Publication No. WO 91/00353, the performance characteristics and problems associated with liquefaction with wild type *Bacillus licheniformis* α-amylase are approached by genetically engineering the α-amylase to include the specific substitions Ala-111-Thr, His-133-Tyr and/or Thr-149-lle.

Studies using recombinant DNA techniques to explore which residues are important for the catalytic activity of amylases and/or to explore the effect of modifying certain amino acids within the active site of various amylases and glycosylases have been conducted by various researchers (Vihinen et al., J. Biochem., vol. 107, pp. 267-272 (1990); Holm et al., Protein Engineering, vol. 3, pp. 181-191 (1990); Takase et al., Biochemica et Biophysica Acta, vol. 1120, pp. 281-288 (1992); Matsui et al., Febs Letters, vol. 310, pp. 216-218 (1992); Matsui et al., Biochemistry, vol. 33, pp. 451-458 (1992); Sogaard et al., J. Biol. Chem., vol. 268, pp. 22480-22484 (1993); Sogaard et al., Carbohydrate Polymers, vol. 21, pp. 137-146 (1993); Svensson, Plant Mol. Biol., vol. 25, pp. 141-157 (1994); Svensson et al., J. Biotech. vol 29, pp. 1-37 (1993)). Researchers have also studied which residues are important for thermal stability (Suzuki et al., J. Biol. Chem. vol. 264, pp. 18933-18938 (1989); Watanabe et al., Eur. J. Biochem. vol. 226, pp. 277-283 (1994)); and one group has used such methods to introduce mutations et various histidine residues in a *Bacillus licheniformis* amylase, the rationale being that *Bacillus licheniformis* amylase which is known to be relatively thermostable when compared to other similar *Bacillus* amylases, has an excess of histidines and, therefore, it was suggested that replacing a histidine could affect the thermostability of the enzyme. This work resulted in the identification of stabilizing mutations at the histidine residue at the+133 position and the alanine residue at position+209 (Declerck et al., J. Biol. Chem., vol. 265, pp. 15481-15488 (1990); FR 2 665 178-A1; Joyet et al., Bio/Technology, vol. 10, pp. 1579-1583 (1992)).

Despite the advances made in the prior art, a need exists for an α-amylase which is effective enough at low pH values to allow commercial liquefaction at lower pH than currently practical. Similarly, a need exists in the art for a method which allows efficient liquefaction of dry milled grain at high temperatures. Further, a need exists in the art for a method which allows the efficient liquefaction of starch with a decreased reliance on the costly addition of calcium. Additionally, a need exists for a more efficient enzyme to effect a more complete hydrolysis of starch at the liquefaction stage to ensure efficient saccharification. Because commercially available amylases are not acceptable under many conditions due to stability problems, for example, the high alkalinity and oxidant (bleach) levels associated with detergents, there is a need for an amylase having altered, and preferably increased, performance profiles under such conditions. Thus, altered performance characteristics such as increased activity, thermostability, pH stability, oxidative stability or calcium stability which can be achieved while also altering, maintaining, or increasing enzymatic activity as compared to the wild type or precursor enzyme, would be desirable.

SUMMARY OF THE INVENTION

It is an object of the present invention to provide an α-amylase having altered performance profiles, such as pH stability, alkaline stability, oxidative stability or enzymetic activity.

It is a further object of the present invention to provide an α-amylase having increased stability in the absence of added calcium ion during liquefaction of starch.

It is a further object of the present invention to provide an α-amylase having altered low pH stability for use in efficient low pH liquefaction.

It is yet a further object of the present invention to provide an α-amylase which allows efficient liquefaction of dry milled grain at high temperatures.

It is still a further object of the present invention to provide an α-amylase which is useful in high pH environments or in the presence of oxidants or bleach.

It is still a further object of the present invention to provide an α-amylase which effects a more complete hydrolysis of starch molecules to increase the efficiency of saccharification.

According to the present invention, an α-amylase is provided that is the expression product of a mutated DNA sequence encoding an α-amylase, the mutated DNA sequence being derived from a precursor α-amylase by the deletion or substitution of one or more asparagine residues.

Preferably, the deleted or substituted asparagine residue is at a position corresponding to N188 in *Bacillus licheniformis*. Where it is desired to alter the thermostability of the α-amylase, the asparagine substitution may be any other amino acid, including any of the 20 naturally occurring amino acids. Preferably, the substitution corresponds to N188S in *Bacillus licheniformis* when improved stability under liquefaction conditions is desired. Also preferably, the α-amylase further comprises the deletion or substitution of a methionine or tryptophan residue.

BRIEF DESCRIPTION OF THE DRAWINGS

FIG. 1 illustrates mutagenic oligonucleotides useful during directed mutagenesis of Asn188 from *Bacillus licheniformis* α-amylase. In this and following figures illustrating oligonucleotide constructs, bold letters indicate base changes introduced by the oligonucleotide and underlining indicates restriction endonuclease sites introduced by the oligonucleotide.

FIG. 2 illustrates PCR primers used for PCR processing of mutagenic oligonucleotide templates.

FIG. 3 illustrates the DNA sequence of the gene for α-amylase from *Bacillus licheniformis* (NCIB 8061) (SEQ ID NO:33) and deduced amino acid sequence of the translation product (SEQ ID NO:41) as described by Gray et al., J. Bacteriology, vol. 166, pp. 635–643 (1986).

FIG. 4 illustrates the amino acid sequence (SEQ ID NO:34) of the mature α-amylase enzyme from *Bacillus licheriformis*.

FIG. 5 illustrates an alignment of the primary structures of three Bacillus α-amylases. The *Bacillus licheriformis* α-amylase (Am-Lich) (SEQ ID NO:35) is described by Gray et al., J. Bacteriology, vol. 166, pp. 635–643 (1986); the *Bacilus amyloliquefaciens* α-amylase (Am-Amylo) (SEQ ID NO:36) is described by Takkinen et al., J. Biol. Chem., vol. 258, pp. 1007–1013 (1983); and the *Bacillus stearothermophlius* α-amylase (Am-Stearo) (SEQ ID NO:37) is described by Ihara et al., J. Biochem., vol. 98, pp. 95–103 (1985).

FIG. 6 illustrates plasmid pHP13 wherein $Cm^R$ refers to chloramphenicol resistance, $Em^R$ refers to erythromycin resistance and Rep pTA1060 refers to the origin of replication from plasmid pTA1060.

FIG. 7 illustrates the pBLapr plasmid wherein BL AA refers to *Bacillus licheniformis* α-amylase gene; aprE refers to the promoter and signal peptide encoding region of the aprE gene; AmpR refers to the ampicillin resistant gene from pBR322; and CAT refers to the chloramphenicol resistance gene from pC194.

FIG. 8 illustrates the pHPBL plasmid carrying the gene for *Bacillus licheniformis* α-amylase.

FIG. 9 illustrates a schematic of the PCR method used to produce the mutant oligonucleotide primers corresponding to α-amylase derived from *Bacillus lichenformis*.

FIG. 10 illustrates a graph derived from a statistical analysis of variant enzyme according to the invention, M15T/N188S, compared to wild type *Bacillus lichenformis* α-amylase in starch liquefaction at 107° C., 60 ppm calcium and varying pH.

FIG. 11 illustrates a graph derived from a statistical analysis of the performance of a variant enzyme according to the invention, M15T/N188S, compared to wild type *Bacillus licheriformis* α-amylase in starch liquefaction at 107° C., pH 6.0 and varying calcium concentration.

FIG. 12 illustrates a graph derived from a statistical analysis of the performance of a variant enzyme according to the invention, M15T/N188S, compared to wild type *Bacillus licheriformis* α-amylase in starch liquefaction at pH 6.0, 60 ppm calcium and varying temperature.

FIG. 13 illustrates the signal sequence-mature protein junctions in α-amylase derived from *Bacillus licheriformis* (SEQ ID NO:38), *Bacillus subtills* aprE (SEQ ID NO: 39) and *Bacillus licheriformis* in pBLapr (SEQ ID NO:40).

DETAILED DESCRIPTION

"α-Amylase" means an enzymatic activity which cleaves or hydrolyzes the α(1–4)glycosidic bond, e.g., that in starch, amylopectin or amylose polymers. α-Amylase as used herein includes naturally occurring α-amylases as well as recombinant α.amylases. Preferred α-amylases in the present invention are those derived from *Bacillus licherformis*, *Bacillus amyloliquefaciens* or *Bacillus stearothermophilus*, as well as fungal α-amylases such as those derived from Aspergillus (i.e., A. oryzae and A. niger).

"Recombinant α-amylase" means an α-amylase in which the DNA sequence encoding the naturally occurring α-amylase is modified to produce a mutant DNA sequence which encodes the substitution, insertion or deletion of one or more amino acids in the α-amylase sequence compared to the naturally occurring α-amylase.

"Expression vector" means a DNA construct comprising a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *Bacillus subtills* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

"Host strain" or "host cell" means a suitable host for an expression vector comprising DNA encoding the α-amylase according to the present invention. Host cells useful in the present invention are generally procaryotic or eucaryotic hosts, including any transformable microorganism in which the expression of α-amylase according to the present invention can be achieved. Specifically, host strains of the same species or genus from which the α-amylase is derived are suitable, such as a Bacillus strain. Preferably, an α-amylase negative Bacillus strain (genes deleted) and/or an α-amylase and protease deleted Bacillus strain (ΔamyE, Δapr, Δnpr) is used. Host cells are transformed or transfected with vectors constructed using recombinant DNA techniques. Such transformed host cells are capable of either replicating vectors encoding the α-amylase and its variants (mutants) or expressing the desired α-amylase.

"Liquefaction" or "liquefy" means a process by which starch is converted to shorter chain and less viscous dextrins. Generally, this process involves gelatinization of starch simultaneously with or followed by the addition of α-amylase.

According to the present invention, an α-amylase is provided that is the expression product of a mutated DNA sequence encoding an α-amylase, the mutated DNA sequence being derived from a precursor α-amylase by the deletion or substitution of one or more asparagine residues. Also provided is a nucleic acid molecule (DNA) which encodes an amino acid sequence comprising at least a part of the α-amylase provided by the present invention, expression systems incorporating such DNA including vectors and phages, host cells transformed with such DNA, and anti-sense strands of DNA corresponding to the DNA molecule which encodes the amino acid sequence. Similarly, the present invention includes a method for producing an α-amylase by expressing the DNA incorporated on an expression system which has been transformed into a host cell. The α-amylase of the invention may be used in liquefaction of starch, as an ingredient in detergents, in food processing, in textile processing, or in any other application in which α-amylase activity is useful.

The α-amylases according to the present invention comprise an amino acid sequence which is derived from the amino acid sequence of a precursor α-amylase.

The precursor α-amylases include naturally occurring α-amylases and recombinant α-amylases. The amino acid sequence of the α-amylase mutant is derived from the precursor α-amylase amino acid sequence by the substitution, deletion or insertion of one or more amino acids of the precursor amino acid sequence. Such modification is generally of the precursor DNA sequence which encodes the amino acid sequence of the precursor α-amylase rather than manipulation of the precursor α-amylase enzyme per se. Suitable methods for such manipulation of the precursor DNA sequence include methods disclosed herein and in commonly owned U.S. Pat. Nos. 4,760,025 and 5,185,258, incorporated herein by reference.

The α-amylases according to the present invention are derived from a precursor amylase. The precursor α-amylase is produced by any source capable of producing α-amylase. Suitable sources of α-amylases are prokaryotic or eukaryotic organisms, including fungi, bacteria, plants or animals. Preferably, the precursor α-amylase is produced by a Bacillus; more preferably, by *Bacillus lichenformis*, *Bacillus amyloliquefaciens* or *Bacillus stearothermophfius*; most preferably, the precursor α-amylase is derived from *Bacillus lichenformis*.

Homologies have been found between almost all endoamylases sequenced to date, ranging from plants, mammals, and bacteria (Nakajima et al., Appl. Microbiol. Biotechnol., vol. 23, pp. 355–360 (1986); Rogers, Biochem. Biophys. Res. Commun., vol. 128, pp. 470–476 (1985); Janecek, Eur. J. Biochem., vol. 224, pp. 519–524 (1994)). There are four areas of particularly high homology in certain Bacillus amylases, as shown in FIG. 5, wherein the underlined sections designate the areas of high homology. Sequence alignments have also been used to map the relationship between Bacillus endo-amylases (Feng et al., J. Molec. Evol., vol. 35, pp. 351–360 (1987)). The relative sequence homology between *Bacillus stearothermophilus* and *Bacillus lichenformis* amylase is about 66% and that between *Bacillus lichenformis* and *Bacillus amyloliquefaciens* amylases is about 81%, as determined by Holm et al., Protein Engineering, vol. 3, No. 3, pp. 181–191 (1990). While sequence homology is important, it is generally recognized that structural homology is also important in comparing amylases or other enzymes. For example, structural homology between fungal amylases and bacterial amylase has been suggested and, therefore, fungal amylases are encompassed within the present invention.

Residues corresponding to asparagine residues in α-amylase are identified herein for deletion or substitution. Thus, specific residues such as N188 refer to an amino acid position number (i.e., +188) which references the number assigned to the mature *Bacillus lichenformis* α-amylase sequence illustrated in FIG. 4. The invention, however, is not limited to the mutation of the particular mature α-amylase of *Bacillus lichenformis* but extends to precursor α-amylases containing amino acid residues at positions which are equivalent to the particular identified residue in *Bacillus lichenformis* α-amylase. A residue of a precursor α-amylase is equivalent to a residue of *Bacillus lichenformis* α-amylase if it is either homologous (i.e., corresponds in position for either the primary or tertiary structure) or analogous to a specific residue or portion of that residue in *Bacillus lichenformis* α-amylase (i.e., having the same or similar functional capacity to combine, react, or interact chemically or structurally).

In order to establish homology to primary structure, the amino acid sequence of a precursor α-amylase is directly compared to the *Bacillus Licheniformis* α-amylase primary sequence and particularly to a set of residues known to be invariant to all α-amylases for which sequences are known (see e.g., FIG. 7). It is possible also to determine equivalent residues by tertiary structure analysis of the crystal structures reported for porcine pancreatic α-amylase (Buisson et al., EMBO Journal, vol. 6, pp. 3909–3916 (1987); Qian et al., Biochemistry, vol. 33, pp. 6284–6294 (1994); Larson et al., J. Mol. Biol., vol. 235, pp. 1560–1584 (1994)); Takaamylase A from *Aspergillus oryzae* (Matsuura et al., J. Biochem. (Tokyo), vol. 95, pp. 697–702 (1984)); and an acid α-amylase from A. niger (Boel et al. Biochemistry, vol. 29, pp. 6244–6249 (1990)), with the former two structures being similar, and for barley α-amylase (Vallee et al., J. Mol. Biol., vol. 236, pp. 368–371(1994); Kadziola, J. Mol. Biol., vol. 239, pp. 104–121 (1994)). Although there have been some preliminary studies published (Suzuki et al, J. Biochem., vol. 108, pp. 379–381 (1990); Lee et al., Arch. Biochem. Biophys, vol. 291, pp. 255–257 (1991); Chang et al, J. Mol. Biol., vol. 229, pp. 235–238 (1993); Mizuno et al., J. Mol. Biol., vol. 234, pp. 1282–1283 (1993)), there is only a published structure for *Bacillus lichenformis* α-amylase (Machius et al., J. Mol. Biol. vol. 246, pp. 545–549 (1995)). However, several researchers have predicted common supersecondary structures between glucanases (MacGregor et el., Biochem. J., vol. 259, pp. 145–152 (1989)) and within α-amylases and other starch-metabolising enzymes (Jespersen, J. Prot. Chem. vol. 12, pp. 791–805 (1993); MacGregor, Starke, vol. 45, pp. 232–237 (1993)); and sequence similarities between enzymes with similar supersecondary structures to α-amylases (Janecek, FEBS Letters, vol. 316, pp. 23–26 (1993); Janecek et al., J. Prot. Chem., vol. 12, pp. 509–514 (1993)). A structure for the *Bacillus stearothermophilus* enzyme has been modeled on that of Taka-amylase A (Holm et al., Protein Engineering, vol. 3, pp. 181–191 (1990)). The four highly conserved regions shown in FIG. 7 contain many residues thought to be part of the active-site (Matsuura et al., J. Biochem. (Tokyo), vol. 95, pp. 697–702 (1984); Buisson et al., EMBO Journal, vol. 6, pp. 3909–3916 (1987); Vihinen et al., J. Biochem., vol. 107, pp. 267–272 (1990)) including His+105; Arg+229; Asp+ 231; His+235; Glu+261 and Asp+328 under the *Bacillus lichenformis* numbering system.

Preferably, the deleted or substituted asparagine residue is at a position corresponding to N188 in *Bacillus lichenformis*. Where it is desired to alter the thermostability of the α-amylase, the asparagine substitution may be any other amino acid, including any of the 20 naturally occurring amino acids. Preferably, the deletion or substitution corresponds to N188S in *Bacillus lichenformis*. Also preferably, the amylase further comprises the deletion or substitution of a methionine or tryptophan residue.

The α-amylases according to the present invention exhibit altered performance characteristics providing desirable and unexpected results which are useful in the various applications for which α-amylases are commonly used. For example, α-amylases according to the present invention which exhibit altered performance characteristics at low pH, including improved thermostability, improved pH stability and/or improved oxidative stability, are useful in low pH liquefaction of starch. Enhanced thermostability will be useful in extending the shelf life of products which incorporate them. Enhanced oxiderive stability or improved performance is particularly desirable in cleaning products, and for extending the shelf life of α-amylase in the presence of bleach, perborate, percarbonate or peracids used in such cleaning products. To the contrary, reduced thermal stability or oxidative stability may be useful in industrial processes which require the rapid and efficient quenching of amylolytic activity.

The α-amylase of the present invention is especially useful in starch processing and particularly in starch liquefaction. Conditions present during commercially desirable liquefaction processes characteristically include low pH, high temperature and potential oxidation conditions requiring α-amylases exhibiting improved low pH performance, improved thermal stability and improved oxidative stability. Accordingly, α-amylases according to the present invention which are particularly useful in liquefaction exhibit improved performance at a pH of less than about 6, preferably less than about 5.5, and most preferably between about 5.0 and 5.5. Additionally, α-amylases according to the present invention which exhibit increased thermal stability at temperatures of between about 80°–120° C., and preferably between about 100°–110° C., and increased stability in the presence of oxidants will be particularly useful. Preferably, the α-amylase according to the present invention which is used in liquefaction, in addition to the deletion or substitution of an asparagine, further comprises a deletion or substitution at a methionine or a tryptophan, and particularly at position M15, W138 and/or M197. In a more preferred embodiment, α-amylase used in starch liquefaction according to the present invention comprises a deletion or substitution at position N188. Most preferably, the amylase is derived from *Bacillus licheniformis* or *Bacillus stearothermophilus* and comprises a substitution corresponding to M15T/N188S.

Additional components known by those skilled in the art to be useful in liquefaction, including, for example, antioxidants, calcium, ions, salts or other enzymes such as endoglycosidases, cellulases, proteases, lipases or other amylase enzymes may be added depending on the intended reaction conditions. For example, combinations of the α-amylase according to the present invention with α-amylases from other sources may provide unique action profiles which find particular use under specific liquefaction conditions. In particular, it is contemplated that the combination of the α-amylase according to the present invention with α-amylase derived from *Bacillus stearothermophilus* will provide enhanced liquefaction at pH values below 5.5 due to complementary action patterns. A preferred embodiment where the process involves the liquefaction of dry milled starch for ethanol production comprises α-amylase derived from *Bacillus stearothermophilus* and α-amylase according to the present invention having the substitution M15T/N188S.

During liquefaction, starch, specifically granular starch slurries from either a wet or dry milled process, is treated with an α-amylase of the present invention according to known liquefaction techniques. Generally, in the first step of the starch degradation process, the starch slurry is gelatinized by heating at a relatively high temperature (between about 80° C. and about 110° C.). After the starch slurry is gelatinized, it is liquefied using an α-amylase.

In another embodiment of the present invention there are provided detergent compositions in either liquid, gel or granular form, which comprise the α-amylase according to the present invention. Such detergent compositions will particularly benefit from the addition of an α-amylase according to the present invention which has increased thermal stability to improve shelf-life or increased oxidative stability such that the α-amylase has improved resistance to bleach or peracid compounds commonly present in detergents. Thus, α-amylase according to the present invention may be advantageously formulated into known powdered, liquid or gel detergents having a pH of between about 6.5 and about 12.0. A preferred embodiment of the present invention further comprises the deletion or substitution of a methionine residue or a tryptophan residue, for example M15, M197 or W138 as described in commonly assigned U.S. patent application Ser. Nos. 08/289,351 and 08/409,771, the disclosures of which are incorporated by reference. Also preferably, an α-amylase according to the present invention used in detergent compositions comprises a deletion or substitution at position N188. Detergent compositions comprising the α-amylase according to the present invention may further include other enzymes such as endoglycosidases, cellulases, proteases, lipases or other amylase enzymes, particularly α-amylase derived from *Bacillus stearothermophilus* as well as additional ingredients as generally known in the art.

Embodiments of the present invention which comprise a combination of the α-amylase according to the present invention with protease enzymes preferably include oxidatively stable proteases such as those described in U.S. Pat. No. Re. 34,606, incorporated herein by reference, as well as commercially available enzymes such as DURAZYM (Novo Nordisk), MAXAPEM (Gist-brocades) and PURAFECT® OxP (Genencor International, Inc.). Methods for making such protease mutants (oxidatively stable proteases), and particularly such mutants having a substitution for the methionine at a position equivalent to M222 in *Bacillus amyloliquefaciens*, are described in U.S. Pat. No. Re. 34,606.

An additional embodiment of the present invention comprises DNA encoding an α-amylase according to the present invention and expression vectors comprising such DNA. The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose. In addition, any of a wide variety of expression control sequences are generally used in these vectors. For example, Applicants have discovered that a preferred expression control sequence for Bacillus transformants is the aprE signal peptide derived from *Bacillus subfills*.

A wide variety of host cells are also useful in expressing the DNA sequences of this invention. These hosts may include well known eukaryotic and prokaryotic hosts, such as strains of *E. coil, Pseudomonas, Bacillus, Streptomyces*, various fungi, yeast and animal cells. Preferably, the host expresses the α-amylase of the present invention extracellularly to facilitate purification and downstream processing. Expression and purification of the mutant α-amylase of the invention may be effected through art-recognized means for carrying out such processes.

The improved α-amylases according to the present invention provide several important advantages when compared to wild type Bacillus α-amylases. For example, one advantage is the increased activity found at low pH and high temperatures typical of common starch liquefaction methods. Another advantage is the increased high pH and oxidative stability which facilitates their use in detergents. Another advantage is that a more complete hydrolysis of starch molecules is achieved which reduces residual starch in the processing stream. Yet another advantage is their improved stability in the absence of calcium ion. Yet another advantage is that the addition of equal protein doses of α-amylase according to the invention provide superior performance when compared to wild type *Bacillus lichenformis* α-amylase due to improvements in both specific activity and stability under stressed conditions. In other words, because of the generally increased stability of the amylases according to the present invention, the increased specific activity on starch of the inventive amylases translates to even greater potential performance benefits of this variant. Under conditions where the wild type enzyme is being inactivated, not only does more of the inventive amylase survive because of its increased stability, but also that which does survive expresses proportionally more activity because of its increased specific activity.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

EXAMPLES

Example 1
Construction Of Plasmid pHP.BL

The α-amylase gene shown in FIG. 3 was cloned from *Bacillus lichenformis* NCIB8061 (Gray et al., J. Bacteriology, vol. 166, pp. 635–643 (1986)). The 1.72kb PstI-SstI fragment, encoding the last three residues of the signal sequence, the entire mature protein and the terminator region, was subcloned into M13mpl 8. A synthetic terminator was added between the BclI and SstI sites using a synthetic oligonucleotide cassette of the form:

BclI 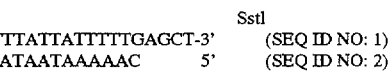 SstI
5'-GATCAAAACATAAAAAACCGGCCTTGGCCCCGCCGGTTTTTTATTATTTTTGAGCT-3'   (SEQ ID NO: 1)
3'    TTTTGTATTTTTTGGCCGGAACCGGGGCGGCCAAAAAATAATAAAAAC        5'   (SEQ ID NO: 2)

designed to contain the *Bacillus amyloliquefaciens* subtilisin transcriptional terminator (Wells et al., Nucleic Acid Research, vol. 11, pp. 7911–7925 (1983)).

The pBLapr plasmid was constructed carrying the gene for the *Bacillus licheniformis* α-amylase. As illustrated in FIG. 7, pBLapr comprises a 6.1kb plasmid including the ampicillin resistance gene from pBR322 and the chloramphenicol resistance gene from pC194, the aprE promoter and the gene encoding for the *Bacillus licheniformis* α-amylase ("BL AA"). The aprE promoter was constructed from a 660bp HindIII-PstI fragment encoding for the promoter and signal sequence of the *Bacillus subtilis* alkaline protease. The PstI site was removed, and an SfiI site added close to the aprE/BL AA junction. The BL AA gene comprises the 1720 bp PstI-SstI fragment described above. In the work described herein, pBLapr was constructed with an SfiI site adjacent to the 5' end of the start of the coding sequence for the mature amylase gene. Specifically, the 5' end of the pBLapr construction was subcloned on an EcoRI-SstII fragment from pBLapr into M13BM20 (Boehringer Mannheim) to obtain a coding-strand template for the mutagenic oligonucleotide below: 5'-CCC ATT AAG ATT GGC CGC CTG GGC CGA CAT GTT GCT GG-3' (SEQ ID NO:3) This primer introduced an SfiI site (indicated by underlining) which allowed correct forms to be screened for by the presence of this unique restriction site. Subcloning the EcoRI-SstII fragment back into the pBLapr vector gave a version of the plasmid containing an SfiI site.

Plasmid pHP13 (Haima et al., Mol. Gert. Genet., vol. 209, pp. 335–342 (1987)) (FIG. 6) was digested with restriction enzymes EcoRI and HindIII and the resulting vector purified on a polyacrymide gel and then eluted. Plasmid pBLapr was digested with HindIII, Asp718 and in a separate incubation with Asp718, EcoRI and gel purified. Two bands, HindIII-Asp718 (1203 bp) and Asp718-EcoRI (1253 bp) were gel purified, eluted from the gel and ligated into the vector by a 3-way ligation, to give plasmid pHP.BL, the plasmid used in expression of the α-amylase (FIG. 8).

Example 2
Construction Of Plasmid Encoding α-Amylase Comprising Substitutions For Asparagine 188

A series of mutagenic primers encoding for substitutions of Asn188 ("N188") with each of the naturally occurring amino acids were synthesized and are shown in FIG. 1 (SEQ ID NOS:4–22). The α-amylase gene mutations encoding for these changes were made by PCR, according to the procedure summarized in FIG. 9, using the PCR primers shown in FIG. 2 (SEQ ID NOS:23–32).

Step (1):

The mutagenic primers were used as templates for the PCR primers PCR A+ and PCR B– resulting in a lengthened (61 bp) double stranded DNA. Each contained a different amino acid replacement at position 188, and all except N188M contained a different restriction site. Initially the PCR primers were annealed at 35° C. for five minutes followed by a one minute DNA extension with tag polymerase at 75° C. The double stranded DNA was then melted at 95° C. for one minute, followed by the annealing and extension steps. Melting, annealing and extension continued for a total of 30 cycles.

Step (2):

DNA upstream and downstream of position 188 were made in separate PCR reactions. The template was pBLapr, and the PCR primers were LAAfs5 (SEQ ID NO:27) and PCR A– (SEQ ID NO:24) for upstream; and PCR B+(SEQ ID NO:25) and PCR CIa-SalI (SEQ ID NO:28) for downstream DNA. The DNA was melted at 95° C. for one minute, annealed at 45° C. for three minutes and elongated at 68° C. for 3 minutes. The upstream portion is 290 bp and downstream is 498 bp. This procedure was repeated for 18 cycles using pfu polymerase. The same PCR procedure was used in steps (3) and (4).

Step (3):

The upstream portion of DNA described in step (2) was attached to the double stranded mutagenic primers described in step (1). Primers LAAfs5 (SEQ ID NO:27) and PCR B– (SEQ ID NO:26) were used. As the result of primer design there is a 24 bp overlap between these templates allowing for the attachment of the two pieces of DNA.

Step (4):

The downstream portions of DNA described in Step (2) and the product of Step (3) were attached to give the final product. A 24 bp overlap between the two PCR products allows for the attachment. Primers used were LAAfs5 (SEQ ID NO:27) and PCR ClaI-SalI (SEQ ID NO:28).

Step (5):

Unique restriction sites, Asp718 and BssHII, are located upstream and downstream, respectively, of the 188 site. The final PCR product is digested with Asp718 and BssHII, the 333 bp fragment isolated by polyacrylamide gel electrophoresis and subcloned into the pHP.BL vector to obtain pHP.N188X.

Mutations were confirmed by dideoxy sequencing (Sanger et al., Proc. Natl. Acad. Sci. U.S.A., vol. 74, pp. 5463–5467 (1977)).

With reference to the DNA sequence and numbering system used in FIG. 3, the codon encoding for the+188 amino acid position is at base pairs 812–814. PCR primers A+ and A– correspond to base pairs 784–807. PCR primers B+ and B– correspond base pairs 821–844. The 5' end of PCR primer LAAfs5 corresponds to base pair 518. The 5' end of PCR primer PCR ClaI-SalI corresponds to base pair 1317. The Asp718 site corresponds to base pair 724. The BssHII site corresponds to base pair 1053.

Example 3
Construction Of Plasmid Encoding Mutations At M15 And N188

A pBLapr plasmid having threonine substituted for methionine at amino acid 15 was constructed according to U.S. patent application Ser. No. 08/194,664 (PCT Publication No. WO 94/18314). This plasmid (pBLaprM15T) was digested with SfiI and Asp718, and the 477 base pair fragment subcloned into pHP.BL to create pHP.M15T. In a manner analogous to that described above, Example 1, pHP.M15T was digested with Asp718 and BssHII, gel purified and eluted from the gel. The 333 base pair fragment comprising Asp718 to BssHII and the fragment from pHP.N188S were then subcloned into pHP.M15T to give plasmid pHP.M15T/N188S. In an analogous manner, starting with plasmids pBL aprM15L and pHP.N188Y, the plasmid pHP.M15L/N188Y was constructed.

Example 4
Transformation Of Plasmids Into *Bacillus subtills*, Expression And Purification of Mutant α-Amylase α-Amylase was expressed in *Bacillus subtills* after transformation with the plasmids described in Examples 1–3. pHP13 is a plasmid able to replicate in *E. coil* and in *Bacillus subtills*. Plasmids containing different variants were constructed using *E. coil* strain MM294, the plasmids isolated and then transformed into *Bacillus subtills* as described in Anagnostopoulos et al., J. Bacter., vol. 81, pp. 741–746 (1961). The Bacillus strain had been deleted for two proteases (Δapr, Δnpr) (see e.g., Ferrari et al., U.S. Pat. No. 5,264,366) and for amylase (ΔamyE) (see e.g., Stahl et al., J. Bacter., vol. 158, pp. 411–418 (1984)). The bacillus strain expressing M15L/N188Y was found to form larger zones of clearing than the strain expressing M15L on agar plates containing 1% insoluble starch indicating increased amylolytic activity. After transformation, the sacU(Hy) mutation (Henner et al., J. Bacter., vol., 170, pp. 296–300 (1988)) was introduced by PBS-1 mediated transduction (Hoch, J. Bact., vol. 154, pp. 1513–1515 (1983)).

Secreted amylases were routinely recovered from *Bacillus subtills* cultures as follows: The culture supernatant was adjusted to 20% saturated ammonium sulfate and stirred for one hr. at 4° C. After centrifugation, the resultant supernatant was adjusted to 70% saturated ammonium sulfate and stirred for one hr. at 4° C. After centrifugation of the supernatant, the resultant pellet was re-dissolved in 50mM sodium acetate, pH 6.0, 5 mM calcium chloride, and sterile filtered.

Example 5
Assay For Determining α-Amylase Activity

Soluble Substrate Assay:

A rate assay was developed based on an end-point assay kit supplied by Megazyme (Aust.) Pty. Ltd. A vial of substrate (p-nitrophenyl maltoheptaoside, BPNPG7) was dissolved in 10 ml of sterile water followed by a 1:4 dilution in assay buffer (50 mM maleate buffer, pH 6.7, 5 mM calcium chloride, 0.002% Tween20). Assays were performed by adding 10 µl of amylase to 790 µl of the substrate in a cuvette at 25° C. Rates of hydrolysis were measured as the rate of change of absorbance at 410nm, after a delay of 75 seconds. The assay was linear up to rates of 0.2 absorption units/min.

α-Amylase protein concentration was measured using the standard Bio-Rad Assay (Bio-Rad Laboratories) based on the method of Bradford, Anal. Biochem., vol. 72, p. 248 (1976) using bovine serum albumin standards.

Starch Hydrolysis Assay:

α-Amylase activity on starch was determined through an assay which depends on the ability of starch to form a blue colored complex with iodine and the disappearance of this color when starch is hydrolyzed to shorter dextrin molecules. The α-amylase activity was defined in terms of the digestion time required to produce a color change denoting a definite state of dextrination of the starch.

Reagents used were as follows:

Phosphate buffer—Potassium dihydrogen phosphate (340 g) and sodium hydroxide (25.3 g) were dissolved in water and diluted to ~ two liters. The buffer was cooled to room temperature and the pH was adjusted to 6.2±0.1. The buffer was diluted to two liters in a volumetric flask.

Starch substrate—Ten grams (dry substance) of soluble lintner starch were suspended in 50 ml of water and washed into ~300 ml of boiling water. The suspension was again brought to boiling and was boiled for five minutes with constant stirring. The starch solution was cooled with constant stirring to room temperature and 125 ml of phosphate buffer was added. The solution was diluted to 500 ml with water. The starch substrate was made fresh daily.

Stock iodine solution—Iodine crystals (5.5 g) and potassium iodide (11.0 g) were dissolved in water and were volumetrically diluted to 250 ml. The solution was kept from light.

Dilute iodine solution—Potassium iodide (20 g) and two ml of stock iodine solution were dissolved in water and diluted volumetrically to 500 ml. The solution was made fresh daily.

Enzyme diluting solution—Calcium chloride (11.1 g) was dissolved in four liters of water. Water used for all reagents was either distilled or deionized.

An α-amylase sample was diluted to between 10–15 LU/ml (as defined below) with enzyme diluting solution. For many commercial α-amylase preparations a suitable dilution was found to be 2000 fold. Five milliliter aliquots of dilute iodine solution were dispensed into 13×100 mm test tubes and 10 ml of starch substrate was placed in a 23×200 mm test tube. All tubes were placed in the 30° C. water bath. A Hellige comparator equipped with a special α-amylase color disc (catalog number 620-s5) was used to make readings. Five milliliters of diluted enzyme (also at 30° C.) were mixed with the starch substrate and timing was begun. At appropriate time intervals, for example one minute intervals early in the reaction and 15 second intervals later in the reaction, one ml aliquots of the enzyme-substrate mixture were transferred to a tube containing the dilute iodine solution. The starch iodine solution was mixed and transferred to a 13 mm precision square tube and the color was compared with the standard α-amylase color disc in the Hellige comparator. When the time of the end point was approached, samples were taken at 0.25 minute intervals.

The time required for the colors of the samples and the color disc to match were recorded and the activity (in liquefons per gram or ml) was calculated according to the formula:

$$LU/ml \text{ or } LU/g = \left\{ \frac{570}{V \times t} \right\} \times D$$

Where:

LU=liquefon unit

V=volume of enzyme (5 ml or grams)

t=dextrinization time (minutes)

D=dilution factor:dilution volume divided by ml or g of enzyme diluted.

Mutant α-amylases according to the invention prepared as in Examples 1–4 were tested for their specific activity on starch and soluble substrate. The results, as shown in Table 1, illustrate that mutant amylase according to the invention provides a superior activity profile in comparison with the AA20 wild type α-amylase on both substrates.

TABLE 1

Specific Activity Of Certain α-Amylases On Soluble Substrate And Starch As Percentage Of Wild Type Activity

| α-AMYLASE | Soluble Substrate Assay | Starch Hydrolysis Assay |
| --- | --- | --- |
| Spezyme ® AA20 | 100 | 100 |
| M15T/N188S | 212 | 166 |

Example 6
Starch Liquefaction Conditions—Determination Of Liquefied Starch DE (Dextrose Equivalent)

Starch liquefaction was performed using a reactor composed of 50 feet of 0.24 inch diameter (0.21 inch i.d.) stainless steel tubing bent into an approximately 10 inch diameter coil ~5.5 inches high. The coil was equipped with an 11.5 inch in-line static mixer (Cole-Parmer #G-04669-60) mounted ~4 feet from the anterior end. The posterior end of the coil was equipped with a Swagelok in-line adjustable pressure relief value (#SS-4CA-3) set at a cracking pressure of about 20 psi. Starch slurry was fed to the coil at a rate of ~70 ml/minute with a piston metering pump. The temperature of the reactor coil was held at 105.5° C. by immersion of the reactor in a glycerol-water bath. Temperature in the bath was maintained using a circulating heater\temperature controller (Fisher Scientific model 7305).

Starch liquefaction at the pilot scale was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve. Starch was introduced into the jet at about 350 ml/min. The jet temperature was held at 105°–107° C. Samples of starch were transferred from the jet cooker to a 95° C. second stage liquefaction and held for 90 minutes.

Granular starch was obtained from a corn wet miller and used within two days. The starch was diluted to a desired solids level of about 30–35% dry solids with deionized water and the pH was adjusted with 2.5% NaOH or 6% HCl as required. Calcium was added in the form of $CaCl_2 \cdot 2H_2O$. Typical liquefaction conditions were:

| Starch | 30%–35% solids |
| --- | --- |
| Calcium | 40–60 ppm (30 ppm added) |
| pH | 5.0–6.0 |
| α-amylase | 12–14 LU/g of carbohydrate (dry basis) |

Samples of starch were transferred from the reactor to a 95° C. second stage liquefaction bath and held for 90 minutes. The degree of starch liquefaction was measured immediately after the second stage liquefaction by determining the dextrose equivalent (DE) of the sample according to the method described in the *Standard Analytical Methods of the Member Companies of the Corn Refiners Association, Inc.*, sixth ed., Analytical Procedure Committee (1980).

Example 7
Comparison Of M15T/N188S And Wild Type α-Amylase In Liquefaction at 105.5° C.

α-Amylase comprising the substitution M15T/N188S made as per Examples 1–4 was compared with wild type α-amylase derived from *Bacillus licheniformis* (Spezyme® AA20, available commercially from Genencor International, Inc.) in liquefaction at 105.5° C. As shown in Table 2, the mutant enzymes provided significantly increased performance in jet-liquefaction of starch, especially at low pH. Pilot scale liquefaction was performed with a primary stage liquefaction at 105.5° C. and a secondary stage liquefaction at 95° C. Amylase was added at 12 LU/g of carbohydrate (dry basis).

TABLE 2

Comparative Liquefaction Performance Of α-Amylases At 105.5° C.

| AMYLASE | pH | DE |
| --- | --- | --- |
| Spezyme ® AA20 (Average of Two Runs) | 6.0 | 9.85 |
| G11 (Average of Four Runs) | 6.0 | 12.2 |
| Spezyme ® AA20 | 5.5 | 5.4 |
| G11 (Average of Two Runs) | 5.5 | 8.7 |
| Spezyme ® AA20 | 5.2 | 1.8 |
| G11 | 5.2 | 3.0 |

Example 8
Comparison Of M15T/N188S And Wild Type α-Amylase In Liquefaction at 107.0° C.

α-Amylase comprising substitution M15T/N188S made as per Examples 1–4 was compared with wild type α-amylase derived from *Bacillus licheniformis* (Spezyme® AA20, available commercially from Genencor International, Inc.) in liquefaction at 107° C. As shown in Table 3, the mutant enzymes provided significantly increased performance in jet-liquefaction of starch especially at low pH, as shown by the DE value, during liquefaction processes. Pilot scale liquefaction was performed with a primary stage liquefaction at 107° C. and a secondary stage liquefaction at 95° C. Amylase was added at 12 LU/g or carbohydrate (dry basis).

TABLE 3

Comparative Liquefaction Performance of α-Amylase At 107° C.

| VARIANT | pH  | DE   |
|---------|-----|------|
| AA20    | 6.0 | 7.4  |
| G11     | 6.0 | 11.6 |
| AA20    | 5.5 | 3.5  |
| G11     | 5.5 | 6.0  |
| AA20    | 5.2 | 0    |
| G11     | 5.2 | 1.1  |

Example 9
Statistical Analysis of Liquefaction Results for Mutant and Wild Type α-Amylase The relative liquefaction performance of Spezyme® AA20 and the M15T/N188S variant were extensively explored in a statistical design experiment. Using the "X-STAT" program, Version 2.0 (Copyright, Wiley Scientific and Technical Software, John Wiley & Sons, New York, (1992)), a Box-Behnken factorial experiment was designed; varying the primary liquefaction temperature from 106° C. to 110° C., the liquefaction pH from pH 5.3 to pH 6.0, and the total calcium level in the starch substrate from 30 ppm to 90 ppm. The data in Tables 4 and 5 which formed the basis of this experiment was generated in 15 pilot scale liquefactions each, using 12 LU/gram dry solid substrate of Spezyme® AA20 and M15T\N188S. The data was then fitted to quadratic models. For the M15T/N188S variant, the data fitted the equation DE=842.41+28.374×pH−17.557× Temperature+1.5005×Calcium concentration+1.6243 (pH× Temperature)−0.081506 (pH×Calcium concentration)− 0.0092099 (Temperature×Calcium concentration)−16.841 $(pH)^2$+0.038379 $(Temperature)^2$−0.000124 (Calcium concentration)$^2$ with a standard error about the regression of 1.313 and an explained variation about the mean $(R)^2$ of 93.99%. For Spezyme® AA20, the data was fitted to the equation DE=−652.0+(132.35×pH)+(4.716×Temperature)+ (1.3989×Calcium concentration)−0.050515 (pH× Temperature)−0.019603 (pH×Calcium concentration) −0.011118 (Temperature×Calcium concentration)−10.206 $(pH)^2$+0.02104 $(Temperature)^2$−0.000522 (Calcium concentration)$^2$. With a standard error about the regression of 0.5772 and an explained variation about the mean $(R^2)$ of 98.69%, these equations were used to prepare curves plotting calculated DE vs. pH, vs. Calcium concentration vs. Temperature. Two dimensional representations of that data at 107° C. and 60 ppm Ca+are illustrated in FIGS. 10–12 respectively. As shown in FIGS. 10–12, the mutant amylase outperforms the wild type amylase by enabling more efficient liquefaction of starch at lower pH, lower levels of calcium and higher temperature.

TABLE 4

| pH   | Temperature Celsius | Calcium ppm | Observed Dextrose Equivalent M15T/N188S |
|------|---------------------|-------------|-----------------------------------------|
| 6.00 | 110.2               | 60.0        | 9.8                                     |
| 6.00 | 105.9               | 60.0        | 11.7                                    |
| 5.30 | 110.2               | 60.0        | 2.1                                     |
| 5.30 | 106.5               | 60.0        | 8.1                                     |
| 6.00 | 108.0               | 90.0        | 11.3                                    |
| 6.00 | 107.6               | 30.0        | 10.3                                    |
| 5.30 | 108.4               | 90.0        | 5.9                                     |
| 5.30 | 108.5               | 30.0        | 1.7                                     |
| 5.65 | 110.2               | 90.0        | 9.5                                     |
| 5.65 | 109.8               | 30.0        | 9.9                                     |
| 5.65 | 106.0               | 90.0        | 11.9                                    |
| 5.65 | 105.5               | 30.0        | 9.9                                     |
| 5.65 | 107.8               | 60.0        | 9.5                                     |
| 5.65 | 108.1               | 60.0        | 9.6                                     |
| 6.00 | 108.3               | 60.0        | 11.6                                    |

TABLE 5

| pH   | Temperature Celsius | Calcium ppm | Observed Dextrose Equivalent Spezyme ® AA20 |
|------|---------------------|-------------|---------------------------------------------|
| 6.00 | 110.0               | 60          | 7.4                                         |
| 6.00 | 106.2               | 60          | 9.9                                         |
| 5.30 | 109.7               | 60          | 0.6                                         |
| 5.30 | 105.8               | 60          | 2.9                                         |
| 6.00 | 108.3               | 90          | 8.5                                         |
| 6.00 | 108.4               | 30          | 7.8                                         |
| 5.30 | 108.6               | 90          | 1.2                                         |
| 5.30 | 107.5               | 30          | 0.4                                         |
| 5.65 | 110.0               | 90          | 4.1                                         |
| 5.65 | 109.5               | 30          | 4.0                                         |
| 5.65 | 106.8               | 90          | 8.6                                         |
| 5.65 | 106.0               | 30          | 6.4                                         |
| 5.65 | 107.8               | 60          | 6.1                                         |
| 5.65 | 109.0               | 60          | 5.9                                         |
| 5.65 | 109.0               | 60          | 5.9                                         |

While the invention has been described in terms of various preferred embodiments, the skilled artisan will appreciate that various modifications, substitutions, omissions and changes may be made without departing from the spirit and scope thereof. Accordingly, it is intended that the scope of the present invention be limited solely by the scope of the following claims, including equivalents thereof.

We claim:

1. An α-amylase derived from Bacillus in that it is the expression product of a mutated Bacillus DNA, sequence encoding an α-amylase, the mutated DNA said α-amylase comprising the deletion or substitution of a residue corresponding to N188 in Bacillus lichenformis.

2. The α-amylase according to claim 1, wherein said α-amylase comprises a substitution corresponding to N188S in Bacillus licheniformis.

3. The α-amylase according to claim 1, wherein said deletion or substitution further comprises the deletion or substitution of a methionine or tryptophan residue.

4. The α-amylase according to claim 3, wherein said deletion or substitution of said methionine or tryptophan residue comprises a substitution or deletion corresponding to M15, W138 or M197 in Bacillus lichenformis.

5. The α-amylase according to claim 4, wherein said substitution of said methionine residual comprises a substitution corresponding to M15T, W138 or M197T in Bacillus lichenformis.

6. A DNA encoding the α-amylase according to claim 1.
7. A DNA encoding the α-amylase according to claim 3.
8. A DNA encoding the α-amylase according to claim 4.
9. A DNA encoding the α-amylase according to claim 4.
10. A DNA encoding the α-amylase according to claim 1.
11. An expression vector comprising the DNA of claim 6.
12. An expression vector comprising the DNA of claim 7.
13. An expression vector comprising the DNA of claim 8.
14. An expression vector comprising the DNA of claim 9.
15. An expression vector comprising the DNA of claim 10.
16. A host cell transformed with the expression vector of claim 11.
17. A host cell transformed with the expression vector of claim 12.
18. A host cell transformed with the expression vector of claim 13.
19. A host cell transformed with the expression vector of claim 14.
20. A host cell transformed with the expression vector of claim 15.
21. An α-amylase according to claim 1 having enhanced low pH performance.
22. A detergent composition comprising the α-amylase according to claim 1.
23. The detergent composition according to claim 22, wherein said detergent is useful in laundering soiled fabric.
24. The detergent composition according to claim 22, wherein said detergent is useful in washing soiled dishes.
25. An α-amylase derived from Bacillus comprising the substitutions corresponding to M15T/N188S in Bacillus lichenformis.

* * * * *

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear (i i) MOLECULE TYPE: cDNA (x i) SEQUENCE DESCRIPTION: SEQ ID NO: 1:

GATCAAAACA TAAAAACCG GCCTTGGCCC CGCCGGTTTT TTATTATTTT TGAGCT  56

(2) INFORMATION FOR SEQ ID NO: 2:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 2:

CAAAAATAAT AAAAAACCGG CGGGGCCAAG GCCGGTTTTT TATGTTTT  48

(2) INFORMATION FOR SEQ ID NO: 3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 3:

CCCATTAAGA TTGGCCGCCT GGGCCGACAT GTTGCTGG  38

(2) INFORMATION FOR SEQ ID NO: 4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 4:

GGATTGGGAA GTGTCGACTG AAAACGGCAA CTATGAT  37

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 5:

GGATTGGGAA GTTTCCCCAG AAAATGGCAA CTATGAT  37

(2) INFORMATION FOR SEQ ID NO: 6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 6:

GGATTGGGAA GTTTCTAGAG AAAACGGCAA CTATGAT    37

(2) INFORMATION FOR SEQ ID NO: 7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GGATTGGGAA GTTTCCCTCG AGAACGGCAA CTATGAT    37

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GGATTGGGAA GTTTCGGCCG AAAACGGCAA CTATGAT    37

(2) INFORMATION FOR SEQ ID NO: 9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGATTGGGAA GTTTCCGGAG AAAACGGCAA CTATGAT    37

(2) INFORMATION FOR SEQ ID NO: 10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GGATTGGGAA GTTTCCAAGG AAAACGGCAA CTATGAT    37

(2) INFORMATION FOR SEQ ID NO: 11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GGATTGGGAA GTTTCCCAGG AAAATGGCAA CTATGAT    37

(2) INFORMATION FOR SEQ ID NO: 12:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 12:

GGATTGGGAA GTTTCCCAGG AAAATGGCAA CTATGAT    37

( 2 ) INFORMATION FOR SEQ ID NO: 13:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 13:

GGATTGGGAA GTTTCTCATG AAAACGGCAA CTATGAT    37

( 2 ) INFORMATION FOR SEQ ID NO: 14:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 14:

GGATTGGGAA GTTTCCGAAG AGAACGGCAA CTATGAT    37

( 2 ) INFORMATION FOR SEQ ID NO: 15:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 15:

GGATTGGGAA GTTTCCGAGG AGAACGGCAA CTATGAT    37

( 2 ) INFORMATION FOR SEQ ID NO: 16:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO: 16:

GGATTGGGAA GTTTCATATG AAAACGGCAA CTATGAT    37

( 2 ) INFORMATION FOR SEQ ID NO: 17:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear (i i) MOLECULE TYPE: cDNA (x i) SEQUENCE DESCRIPTION: SEQ ID NO: 17:

GGATTGGGAA GTCTCCTGCG AAAACGGCAA CTATGAT　　　　　　　　　　37

(2) INFORMATION FOR SEQ ID NO: 18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 18:

GGATTGGGAA GTTTCCTTCG AAAACGGCAA CTATGAT　　　　　　　　　　37

(2) INFORMATION FOR SEQ ID NO: 19:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 19:

GGATTGGGAA GTTTCGATCG AAAACGGCAA CTATGAT　　　　　　　　　　37

(2) INFORMATION FOR SEQ ID NO: 20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 20:

GGATTGGGAA GTTTCCATGG AAAACGGCAA CTATGAT　　　　　　　　　　37

(2) INFORMATION FOR SEQ ID NO: 21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 21:

GGATTGGGAA GTTTCCTGGG AAAACGGCAA CTATGAT　　　　　　　　　　37

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO: 22:

GGATTGGGAA GTGAGCTCTG AAAACGGCAA CTATGAT 37

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

AGGAAAGGCT TGGGATTGGG AAGT 24

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

ACTTCCCAAT CCCAAGCCTT TCCT 24

(2) INFORMATION FOR SEQ ID NO: 25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GGCAACTATG ATTATTTGAT GTAT 24

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

ATACATCAAA TAATCATAGT TGCC 24

(2) INFORMATION FOR SEQ ID NO: 27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CTTCATTCCC GCGACATTAA C 21

(2) INFORMATION FOR SEQ ID NO: 28:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 28:

GATTCCCTTG TGAGAATAAA AG                                  22

( 2 ) INFORMATION FOR SEQ ID NO: 29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 29:

AATCATGTCA GGGAAAAAAC TGGG                            24

( 2 ) INFORMATION FOR SEQ ID NO: 30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 30:

CCCAGTTTTT TCCCTGACAT GATT                            24

( 2 ) INFORMATION FOR SEQ ID NO: 31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 31:

TTTACGGTAG CTGAATATTG GCAG                            24

( 2 ) INFORMATION FOR SEQ ID NO: 32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 32:

CTGCCAATAT TCAGCTACCG TAAA                            24

( 2 ) INFORMATION FOR SEQ ID NO: 33:

( i ) SEQUENCE CHARACTERISTICS:
        ( A ) LENGTH: 1968 base pairs
        ( B ) TYPE: nucleic acid
        ( C ) STRANDEDNESS: double
        ( D ) TOPOLOGY: linear (i i) MOLECULE TYPE: DNA (genomic)

(x i) SEQUENCE DESCRIPTION: SEQ ID NO: 33:

| | | | | | |
|---|---|---|---|---|---|
| AGCTTGAAGA | AGTGAAGAAG | CAGAGAGGCT | ATTGAATAAA | TGAGTAGAAA | GCGCCATATC | 60 |
| GGCGCTTTTC | TTTTGGAAGA | AAATATAGGG | AAAATGGTAC | TTGTTAAAAA | TTCGGAATAT | 120 |
| TTATACAACA | TCATATGTTT | CACATTGAAA | GGGGAGGAGA | ATCATGAAAC | AACAAAAACG | 180 |
| GCTTTACGCC | CGATTGCTGA | CGCTGTTATT | TGCGCTCATC | TTCTTGCTGC | CTCATTCTGC | 240 |
| AGCAGCGGCG | GCAAATCTTA | ATGGGACGCT | GATGCAGTAT | TTTGAATGGT | ACATGCCCAA | 300 |
| TGACGGCCAA | CATTGGAAGC | GTTTGCAAAA | CGACTCGGCA | TATTTGGCTG | AACACGGTAT | 360 |
| TACTGCCGTC | TGGATTCCCC | CGGCATATAA | GGGAACGAGC | CAAGCGGATG | TGGGCTACGG | 420 |
| TGCTTACGAC | CTTTATGATT | TAGGGGAGTT | TCATCAAAAA | GGGACGGTTC | GGACAAAGTA | 480 |
| CGGCACAAAA | GGAGAGCTGC | AATCTGCGAT | CAAAAGTCTT | CATTCCCGCG | ACATTAACGT | 540 |
| TTACGGGGAT | GTGGTCATCA | ACCACAAAGG | CGGCGCTGAT | GCGACCGAAG | ATGTAACCGC | 600 |
| GGTTGAAGTC | GATCCCGCTG | ACCGCAACCG | CGTAATTTCA | GGAGAACACC | TAATTAAAGC | 660 |
| CTGGACACAT | TTTCATTTTC | CGGGGCGCGG | CAGCACATAC | AGCGATTTTA | AATGGCATTG | 720 |
| GTACCATTTT | GACGGAACCG | ATTGGGACGA | GTCCCGAAAG | CTGAACCGCA | TCTATAAGTT | 780 |
| TCAAGGAAAG | GCTTGGGATT | GGGAAGTTTC | CAATGAAAAC | GGCAACTATG | ATTATTTGAT | 840 |
| GTATGCCGAC | ATCGATTATG | ACCATCCTGA | TGTCGCAGCA | GAAATTAAGA | GATGGGGCAC | 900 |
| TTGGTATGCC | AATGAACTGC | AATTGGACGG | TTTCCGTCTT | GATGCTGTCA | AACACATTAA | 960 |
| ATTTTCTTTT | TTGCGGGATT | GGGTTAATCA | TGTCAGGGAA | AAAACGGGGA | AGGAAATGTT | 1020 |
| TACGGTAGCT | GAATATTGGC | AGAATGACTT | GGGCGCGCTG | GAAAACTATT | TGAACAAAAC | 1080 |
| AAATTTTAAT | CATTCAGTGT | TTGACGTGCC | GCTTCATTAT | CAGTTCCATG | CTGCATCGAC | 1140 |
| ACAGGGAGGC | GGCTATGATA | TGAGGAAATT | GCTGAACGGT | ACGGTCGTTT | CCAAGCATCC | 1200 |
| GTTGAAATCG | GTTACATTTG | TCGATAACCA | TGATACACAG | CCGGGGCAAT | CGCTTGAGTC | 1260 |
| GACTGTCCAA | ACATGGTTTA | AGCCGCTTGC | TTACGCTTTT | ATTCTCACAA | GGGAATCTGG | 1320 |
| ATACCCTCAG | GTTTTCTACG | GGGATATGTA | CGGGACGAAA | GGAGACTCCC | AGCGCGAAAT | 1380 |
| TCCTGCCTTG | AAACACAAAA | TTGAACCGAT | CTTAAAAGCG | AGAAAACAGT | ATGCGTACGG | 1440 |
| AGCACAGCAT | GATTATTTCG | ACCACCATGA | CATTGTCGGC | TGGACAAGGG | AAGGCGACAG | 1500 |
| CTCGGTTGCA | AATTCAGGTT | TGGCGGCATT | AATAACAGAC | GGACCCGGTG | GGCAAAGCG | 1560 |
| AATGTATGTC | GGCCGGCAAA | ACGCCGGTGA | GACATGGCAT | GACATTACCG | GAAACCGTTC | 1620 |
| GGAGCCGGTT | GTCATCAATT | CGGAAGGCTG | GGGAGAGTTT | CACGTAAACG | GCGGGTCGGT | 1680 |
| TTCAATTTAT | GTTCAAAGAT | AGAAGAGCAG | AGAGGACGGA | TTTCCTGAAG | GAAATCCGTT | 1740 |
| TTTTTATTTT | GCCCGTCTTA | TAAATTTCTT | TGATTACATT | TTATAATTAA | TTTTAACAAA | 1800 |
| GTGTCATCAG | CCCTCAGGAA | GGACTTGCTG | ACAGTTTGAA | TCGCATAGGT | AAGGCGGGA | 1860 |
| TGAAATGGCA | ACGTTATCTG | ATGTAGCAAA | GAAAGCAAAT | GTGTCGAAAA | TGACGGTATC | 1920 |
| GCGGGTGATC | AATCATCCTG | AGACTGTGAC | GGATGAATTG | AAAAAGCT | | 1968 |

(2) INFORMATION FOR SEQ ID NO: 34:

(i) SEQUENCE CHARACTERISTICS:
(A) LENGTH: 483 amino acids
(B) TYPE: amino acid
(C) STRANDEDNESS: single
(D) TOPOLOGY: unknown ( i i ) MOLECULE TYPE: protein ( x i ) SEQUENCE DESCRIPTION: SEQ ID NO: 34:

| Ala | Asn | Leu | Asn | Gly | Thr | Leu | Met | Gln | Tyr | Phe | Glu | Trp | Tyr | Met | Pro |
|---|---|---|---|---|---|---|---|---|---|---|---|---|---|---|---|
| 1 | | | | 5 | | | | 10 | | | | | | 15 | |

| Asn | Asp | Gly | Gln | His | Trp | Lys | Arg | Leu | Gln | Asn | Asp | Ser | Ala | Tyr | Leu |
|---|---|---|---|---|---|---|---|---|---|---|---|---|---|---|---|
| | | | 20 | | | | 25 | | | | | 30 | | | |

| Ala | Glu | His | Gly | Ile | Thr | Ala | Val | Trp | Ile | Pro | Pro | Ala | Tyr | Lys | Gly |
|---|---|---|---|---|---|---|---|---|---|---|---|---|---|---|---|
| | | 35 | | | | 40 | | | | | 45 | | | | |

| Thr | Ser | Gln | Ala | Asp | Val | Gly | Tyr | Gly | Ala | Tyr | Asp | Leu | Tyr | Asp | Leu |
|---|---|---|---|---|---|---|---|---|---|---|---|---|---|---|---|
| | 50 | | | | | 55 | | | | | 60 | | | | |

| Gly | Glu | Phe | His | Gln | Lys | Gly | Thr | Val | Arg | Thr | Lys | Tyr | Gly | Thr | Lys |
|---|---|---|---|---|---|---|---|---|---|---|---|---|---|---|---|
| 65 | | | | | 70 | | | | | 75 | | | | | 80 |

| Gly | Glu | Leu | Gln | Ser | Ala | Ile | Lys | Ser | Leu | His | Ser | Arg | Asp | Ile | Asn |
|---|---|---|---|---|---|---|---|---|---|---|---|---|---|---|---|
| | | | | 85 | | | | | 90 | | | | | 95 | |

| Val | Tyr | Gly | Asp | Val | Val | Ile | Asn | His | Lys | Gly | Gly | Ala | Asp | Ala | Thr |
|---|---|---|---|---|---|---|---|---|---|---|---|---|---|---|---|
| | | | 100 | | | | 105 | | | | | 110 | | | |

| Glu | Asp | Val | Thr | Ala | Val | Glu | Val | Asp | Pro | Ala | Asp | Arg | Asn | Arg | Val |
|---|---|---|---|---|---|---|---|---|---|---|---|---|---|---|---|
| | | | 115 | | | | | 120 | | | | | 125 | | |

| Ile | Ser | Gly | Glu | His | Leu | Ile | Lys | Ala | Trp | Thr | His | Phe | His | Phe | Pro |
|---|---|---|---|---|---|---|---|---|---|---|---|---|---|---|---|
| | | 130 | | | | | 135 | | | | | 140 | | | |

| Gly | Arg | Gly | Ser | Thr | Tyr | Ser | Asp | Phe | Lys | Trp | His | Trp | Tyr | His | Phe |
|---|---|---|---|---|---|---|---|---|---|---|---|---|---|---|---|
| 145 | | | | | 150 | | | | | 155 | | | | | 160 |

| Asp | Gly | Thr | Asp | Trp | Asp | Glu | Ser | Arg | Lys | Leu | Asn | Arg | Ile | Tyr | Lys |
|---|---|---|---|---|---|---|---|---|---|---|---|---|---|---|---|
| | | | | 165 | | | | | 170 | | | | | 175 | |

| Phe | Gln | Gly | Lys | Ala | Trp | Asp | Trp | Glu | Val | Ser | Asn | Glu | Asn | Gly | Asn |
|---|---|---|---|---|---|---|---|---|---|---|---|---|---|---|---|
| | | | 180 | | | | | 185 | | | | | 190 | | |

| Tyr | Asp | Tyr | Leu | Met | Tyr | Ala | Asp | Ile | Asp | Tyr | Asp | His | Pro | Asp | Val |
|---|---|---|---|---|---|---|---|---|---|---|---|---|---|---|---|
| | | 195 | | | | | 200 | | | | | 205 | | | |

| Ala | Ala | Glu | Ile | Lys | Arg | Trp | Gly | Thr | Trp | Tyr | Ala | Asn | Glu | Leu | Gln |
|---|---|---|---|---|---|---|---|---|---|---|---|---|---|---|---|
| | 210 | | | | | 215 | | | | | 220 | | | | |

| Leu | Asp | Gly | Phe | Arg | Leu | Asp | Ala | Val | Lys | His | Ile | Lys | Phe | Ser | Phe |
|---|---|---|---|---|---|---|---|---|---|---|---|---|---|---|---|
| 225 | | | | | 230 | | | | | 235 | | | | | 240 |

| Leu | Arg | Asp | Trp | Val | Asn | His | Val | Arg | Glu | Lys | Thr | Gly | Lys | Glu | Met |
|---|---|---|---|---|---|---|---|---|---|---|---|---|---|---|---|
| | | | | 245 | | | | | 250 | | | | | 255 | |

| Phe | Thr | Val | Ala | Glu | Tyr | Trp | Gln | Asn | Asp | Leu | Gly | Ala | Leu | Glu | Asn |
|---|---|---|---|---|---|---|---|---|---|---|---|---|---|---|---|
| | | | 260 | | | | | 265 | | | | | 270 | | |

| Tyr | Leu | Asn | Lys | Thr | Asn | Phe | Asn | His | Ser | Val | Phe | Asp | Val | Pro | Leu |
|---|---|---|---|---|---|---|---|---|---|---|---|---|---|---|---|
| | | 275 | | | | | 280 | | | | | 285 | | | |

| His | Tyr | Gln | Phe | His | Ala | Ala | Ser | Thr | Gln | Gly | Gly | Gly | Tyr | Asp | Met |
|---|---|---|---|---|---|---|---|---|---|---|---|---|---|---|---|
| | 290 | | | | | 295 | | | | | 300 | | | | |

| Arg | Lys | Leu | Leu | Asn | Gly | Thr | Val | Val | Ser | Lys | His | Pro | Leu | Lys | Ser |
|---|---|---|---|---|---|---|---|---|---|---|---|---|---|---|---|
| 305 | | | | | 310 | | | | | 315 | | | | | 320 |

| Val | Thr | Phe | Val | Asp | Asn | His | Asp | Thr | Gln | Pro | Gly | Gln | Ser | Leu | Glu |
|---|---|---|---|---|---|---|---|---|---|---|---|---|---|---|---|
| | | | | 325 | | | | | 330 | | | | | 335 | |

| Ser | Thr | Val | Gln | Thr | Trp | Phe | Lys | Pro | Leu | Ala | Tyr | Ala | Phe | Ile | Leu |
|---|---|---|---|---|---|---|---|---|---|---|---|---|---|---|---|
| | | | 340 | | | | | 345 | | | | | 350 | | |

| Thr | Arg | Glu | Ser | Gly | Tyr | Pro | Gln | Val | Phe | Tyr | Gly | Asp | Met | Tyr | Gly |
|---|---|---|---|---|---|---|---|---|---|---|---|---|---|---|---|
| | | 355 | | | | | 360 | | | | | 365 | | | |

| Thr | Lys | Gly | Asp | Ser | Gln | Arg | Glu | Ile | Pro | Ala | Leu | Lys | His | Lys | Ile |
|---|---|---|---|---|---|---|---|---|---|---|---|---|---|---|---|
| | 370 | | | | | 375 | | | | | 380 | | | | |

| Glu | Pro | Ile | Leu | Lys | Ala | Arg | Lys | Gln | Tyr | Ala | Tyr | Gly | Ala | Gln | His |
|---|---|---|---|---|---|---|---|---|---|---|---|---|---|---|---|
| 385 | | | | | 390 | | | | | 395 | | | | | 400 |

| Asp | Tyr | Phe | Asp | His | His | Asp | Ile | Val | Gly | Trp | Thr | Arg | Glu | Gly | Asp |
|---|---|---|---|---|---|---|---|---|---|---|---|---|---|---|---|

|     |     |     |     | 405 |     |     |     | 410 |     |     |     | 415 |     |     |
| --- | --- | --- | --- | --- | --- | --- | --- | --- | --- | --- | --- | --- | --- | --- |
| Ser | Ser | Val | Ala | Asn | Ser | Gly | Leu | Ala | Ala | Leu | Ile | Thr | Asp | Gly | Pro |
|     |     |     | 420 |     |     |     |     | 425 |     |     |     | 430 |     |     |
| Gly | Gly | Ala | Lys | Arg | Met | Tyr | Val | Gly | Arg | Gln | Asn | Ala | Gly | Glu | Thr |
|     |     | 435 |     |     |     |     | 440 |     |     |     | 445 |     |     |     |
| Trp | His | Asp | Ile | Thr | Gly | Asn | Arg | Ser | Glu | Pro | Val | Val | Ile | Asn | Ser |
|     | 450 |     |     |     |     | 455 |     |     |     | 460 |     |     |     |     |
| Glu | Gly | Trp | Gly | Glu | Phe | His | Val | Asn | Gly | Gly | Ser | Val | Ser | Ile | Tyr |
| 465 |     |     |     |     | 470 |     |     |     |     | 475 |     |     |     |     | 480 |
| Val | Gln | Arg |

( 2 ) INFORMATION FOR SEQ ID NO: 35:

( i ) SEQUENCE CHARACTERISTICS:
        ( A ) LENGTH: 511 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO: 35:

| Met | Lys | Gln | Gln | Lys | Arg | Leu | Tyr | Ala | Arg | Leu | Leu | Thr | Leu | Leu | Phe |
| --- | --- | --- | --- | --- | --- | --- | --- | --- | --- | --- | --- | --- | --- | --- | --- |
| 1 |     |     |     | 5 |     |     |     | 10 |     |     |     |     |     | 15 |     |
| Ala | Leu | Ile | Phe | Leu | Leu | Pro | His | Ser | Ala | Ala | Ala | Ala | Ala | Asn | Leu |
|     |     |     | 20 |     |     |     |     | 25 |     |     |     |     | 30 |     |     |
| Asn | Gly | Thr | Leu | Met | Gln | Tyr | Phe | Glu | Trp | Tyr | Met | Pro | Asn | Asp | Gly |
|     |     | 35 |     |     |     |     | 40 |     |     |     |     | 45 |     |     |     |
| His | Trp | Lys | Arg | Leu | Gln | Asn | Asp | Ser | Ala | Tyr | Leu | Ala | Glu | His | Gly |
|     | 50 |     |     |     |     | 55 |     |     |     |     |     | 60 |     |     |     |
| Ile | Thr | Ala | Val | Trp | Ile | Pro | Pro | Ala | Tyr | Lys | Gly | Thr | Ser | Gln | Ala |
| 65 |     |     |     |     | 70 |     |     |     |     | 75 |     |     |     |     | 80 |
| Asp | Val | Gly | Tyr | Gly | Ala | Tyr | Asp | Leu | Tyr | Asp | Leu | Gly | Glu | Phe | His |
|     |     |     |     | 85 |     |     |     |     | 90 |     |     |     |     | 95 |     |
| Gln | Lys | Gly | Thr | Val | Arg | Thr | Lys | Tyr | Gly | Thr | Lys | Gly | Glu | Leu | Gln |
|     |     |     | 100 |     |     |     |     | 105 |     |     |     |     | 110 |     |     |
| Ser | Ala | Ile | Lys | Ser | Leu | His | Ser | Arg | Asp | Ile | Asn | Val | Tyr | Gly | Asp |
|     |     |     | 115 |     |     |     |     | 120 |     |     |     | 125 |     |     |     |
| Val | Val | Ile | Asn | His | Lys | Gly | Gly | Ala | Asp | Ala | Thr | Glu | Asp | Val | Thr |
|     |     |     | 130 |     |     |     | 135 |     |     |     |     | 140 |     |     |     |
| Ala | Val | Glu | Val | Asp | Pro | Ala | Asp | Arg | Asn | Arg | Val | Ile | Ser | Gly | Glu |
| 145 |     |     |     |     | 150 |     |     |     |     | 155 |     |     |     |     | 160 |
| His | Leu | Ile | Lys | Ala | Trp | Thr | His | Phe | His | Phe | Pro | Gly | Arg | Gly | Ser |
|     |     |     |     | 165 |     |     |     |     | 170 |     |     |     |     | 175 |     |
| Thr | Tyr | Ser | Asp | Phe | Lys | Trp | His | Trp | Tyr | His | Phe | Asp | Gly | Thr | Asp |
|     |     |     | 180 |     |     |     |     | 185 |     |     |     |     | 190 |     |     |
| Trp | Asp | Glu | Ser | Arg | Lys | Leu | Asn | Arg | Ile | Tyr | Lys | Phe | Gln | Gly | Lys |
|     |     | 195 |     |     |     |     | 200 |     |     |     |     | 205 |     |     |     |
| Ala | Trp | Asp | Trp | Glu | Val | Ser | Asn | Glu | Asn | Gly | Asn | Tyr | Asp | Tyr | Leu |
|     |     | 210 |     |     |     |     | 215 |     |     |     |     | 220 |     |     |     |
| Met | Tyr | Ala | Asp | Ile | Asp | Tyr | Asp | His | Pro | Asp | Val | Ala | Ala | Glu | Ile |
| 225 |     |     |     |     | 230 |     |     |     |     | 235 |     |     |     |     | 240 |
| Lys | Arg | Trp | Gly | Thr | Trp | Tyr | Ala | Asn | Glu | Leu | Gln | Leu | Asp | Gly | Phe |
|     |     |     |     | 245 |     |     |     |     | 250 |     |     |     |     | 255 |     |
| Arg | Leu | Asp | Ala | Val | Lys | His | Ile | Lys | Phe | Ser | Phe | Leu | Arg | Asp | Trp |
|     |     |     | 260 |     |     |     |     | 265 |     |     |     |     | 270 |     |     |

|     |     |     |     |     |     |     |     |     |     |     |     |     |     |     |
|---|---|---|---|---|---|---|---|---|---|---|---|---|---|---|
| Val | Asn | His 275 | Val | Arg | Glu | Lys | Thr 280 | Gly | Lys | Glu | Met | Phe 285 | Thr | Val | Ala |
| Glu | Tyr 290 | Trp | Gln | Asn | Asp | Leu 295 | Gly | Ala | Leu | Glu | Asn 300 | Tyr | Leu | Asn | Lys |
| Thr 305 | Asn | Phe | Asn | His | Ser 310 | Val | Phe | Asp | Val | Pro 315 | Leu | His | Tyr | Gln | Phe 320 |
| His | Ala | Ala | Ser | Thr 325 | Gln | Gly | Gly | Gly | Tyr 330 | Asp | Met | Arg | Lys | Leu 335 | Leu |
| Asn | Gly | Thr | Val 340 | Val | Ser | Lys | His | Pro 345 | Leu | Lys | Ser | Val | Thr 350 | Phe | Val |
| Asp | Asn | His 355 | Asp | Thr | Gln | Pro | Gly 360 | Gln | Ser | Leu | Glu | Ser 365 | Thr | Val | Gln |
| Thr | Trp 370 | Phe | Lys | Pro | Leu | Ala 375 | Tyr | Ala | Phe | Ile | Leu 380 | Thr | Arg | Glu | Ser |
| Gly 385 | Tyr | Pro | Gln | Val | Phe 390 | Tyr | Gly | Asp | Met | Tyr 395 | Gly | Thr | Lys | Gly | Asp 400 |
| Ser | Gln | Arg | Glu | Ile 405 | Pro | Ala | Leu | Lys | His 410 | Lys | Ile | Glu | Pro | Ile 415 | Leu |
| Lys | Ala | Arg | Lys 420 | Gln | Tyr | Ala | Tyr | Gly 425 | Ala | Gln | His | Asp | Tyr 430 | Phe | Asp |
| His | His | Asp 435 | Ile | Val | Gly | Trp | Thr 440 | Arg | Glu | Gly | Asp | Ser 445 | Ser | Val | Ala |
| Asn | Ser | Gly 450 | Leu | Ala | Ala | Leu | Ile 455 | Thr | Asp | Gly | Pro | Gly 460 | Gly | Ala | Lys |
| Arg 465 | Met | Tyr | Val | Gly | Arg 470 | Gln | Asn | Ala | Gly | Glu 475 | Thr | Trp | His | Asp | Ile 480 |
| Thr | Gly | Asn | Arg | Ser 485 | Glu | Pro | Val | Val | Ile 490 | Asn | Ser | Glu | Gly | Trp 495 | Gly |
| Glu | Phe | His | Val 500 | Asn | Gly | Gly | Ser | Val 505 | Ser | Ile | Tyr | Val | Gln 510 | Arg |

(2) INFORMATION FOR SEQ ID NO: 36:

(i) SEQUENCE CHARACTERISTICS:
      (A) LENGTH: 520 amino acids
      (B) TYPE: amino acid
      (C) STRANDEDNESS: single
      (D) TOPOLOGY: unknown (ii) MOLECULE TYPE: protein (xi) SEQUENCE DESCRIPTION: SEQ ID NO: 36:

|     |     |     |     |     |     |     |     |     |     |     |     |     |     |     |     |
|---|---|---|---|---|---|---|---|---|---|---|---|---|---|---|---|
| Met 1 | Arg | Gly | Arg | Gly 5 | Asn | Met | Ile | Gln | Lys 10 | Arg | Lys | Arg | Thr | Val 15 | Ser |
| Phe | Arg | Leu | Val 20 | Leu | Met | Cys | Thr | Leu 25 | Leu | Phe | Val | Ser | Leu 30 | Pro | Ile |
| Thr | Lys | Thr 35 | Ser | Ala | Val | Asn | Gly 40 | Thr | Leu | Met | Gln | Tyr 45 | Phe | Glu | Trp |
| Tyr | Thr 50 | Pro | Asn | Asp | Gly | Gln 55 | His | Trp | Lys | Arg | Leu 60 | Gln | Asn | Asp | Ala |
| Glu 65 | His | Leu | Ser | Asp | Ile 70 | Gly | Ile | Thr | Ala | Val 75 | Trp | Ile | Pro | Pro | Ala 80 |
| Tyr | Lys | Gly | Leu | Ser 85 | Gln | Ser | Asp | Asn | Gly 90 | Tyr | Gly | Pro | Tyr | Asp 95 | Leu |
| Tyr | Asp | Leu | Gly 100 | Glu | Phe | Gln | Gln | Lys 105 | Gly | Thr | Val | Arg | Thr 110 | Lys | Tyr |
| Gly | Thr | Lys | Ser | Glu | Leu | Gln | Asp | Ala | Ile | Gly | Ser | Leu | His | Ser | Arg |

```
              115                      120                       125
    Asn  Val  Gln  Val  Tyr  Gly  Asp  Val  Val  Leu  Asn  His  Lys  Ala  Gly  Ala
         130                      135                      140

Asp  Ala  Thr  Glu  Asp  Val  Thr  Ala  Val  Glu  Val  Asn  Pro  Ala  Asn  Arg
    145                      150                      155                      160

Asn  Gln  Glu  Thr  Ser  Glu  Glu  Tyr  Gln  Ile  Lys  Ala  Trp  Thr  Asp  Phe
                        165                      170                      175

Arg  Phe  Pro  Gly  Arg  Gly  Asn  Thr  Tyr  Ser  Asp  Phe  Lys  Trp  His  Trp
                   180                      185                      190

Tyr  His  Phe  Asp  Gly  Ala  Asp  Trp  Asp  Glu  Ser  Arg  Lys  Ile  Ser  Arg
              195                      200                      205

Ile  Phe  Lys  Phe  Arg  Gly  Glu  Gly  Lys  Ala  Trp  Asp  Trp  Glu  Val  Ser
         210                      215                      220

Ser  Glu  Asn  Gly  Asn  Tyr  Asp  Tyr  Leu  Met  Tyr  Ala  Asp  Val  Asp  Tyr
    225                      230                      235                      240

Asp  His  Pro  Asp  Val  Val  Ala  Glu  Thr  Lys  Lys  Trp  Gly  Ile  Trp  Tyr
                        245                      250                      255

Ala  Asn  Glu  Leu  Ser  Leu  Asp  Gly  Phe  Arg  Ile  Asp  Ala  Ala  Lys  His
                   260                      265                      270

Ile  Lys  Phe  Ser  Phe  Leu  Arg  Asp  Trp  Val  Gln  Ala  Val  Arg  Gln  Ala
              275                      280                      285

Thr  Gly  Lys  Glu  Met  Phe  Thr  Val  Ala  Glu  Tyr  Trp  Gln  Asn  Asn  Ala
         290                      295                      300

Gly  Lys  Leu  Glu  Asn  Tyr  Leu  Asn  Lys  Thr  Ser  Phe  Asn  Gln  Ser  Val
    305                      310                      315                      320

Phe  Asp  Val  Pro  Leu  His  Phe  Asn  Leu  Gln  Ala  Ala  Ser  Ser  Gln  Gly
                        325                      330                      335

Gly  Gly  Tyr  Asp  Met  Arg  Arg  Leu  Leu  Asp  Gly  Thr  Val  Val  Ser  Arg
                   340                      345                      350

His  Pro  Glu  Lys  Ala  Val  Thr  Phe  Val  Glu  Asn  His  Asp  Thr  Gln  Pro
              355                      360                      365

Gly  Gln  Ser  Leu  Glu  Ser  Thr  Val  Gln  Thr  Trp  Phe  Lys  Pro  Leu  Ala
         370                      375                      380

Tyr  Ala  Phe  Ile  Leu  Thr  Arg  Glu  Ser  Gly  Tyr  Pro  Gln  Val  Phe  Tyr
    385                      390                      395                      400

Gly  Asp  Met  Tyr  Gly  Thr  Lys  Gly  Thr  Ser  Pro  Lys  Glu  Ile  Pro  Ser
                        405                      410                      415

Leu  Lys  Asp  Asn  Ile  Glu  Pro  Ile  Leu  Lys  Ala  Arg  Lys  Glu  Tyr  Ala
                   420                      425                      430

Tyr  Gly  Pro  Gln  His  Asp  Tyr  Ile  Asp  His  Pro  Asp  Val  Ile  Gly  Trp
              435                      440                      445

Thr  Arg  Glu  Gly  Asp  Ser  Ser  Ala  Ala  Lys  Ser  Gly  Leu  Ala  Ala  Leu
         450                      455                      460

Ile  Thr  Asp  Gly  Pro  Gly  Gly  Ser  Lys  Arg  Met  Tyr  Ala  Gly  Leu  Lys
    465                      470                           475                 480

Asn  Ala  Gly  Glu  Thr  Trp  Tyr  Asp  Ile  Thr  Gly  Asn  Arg  Ser  Asp  Thr
                        485                      490                      495

Val  Lys  Ile  Gly  Ser  Asp  Gly  Trp  Gly  Glu  Phe  His  Val  Asn  Asp  Gly
                   500                      505                      510

Ser  Val  Ser  Ile  Tyr  Val  Gln  Lys
              515                      520
```

( 2 ) INFORMATION FOR SEQ ID NO: 37:

( i ) SEQUENCE CHARACTERISTICS:
    ( A ) LENGTH: 548 amino acids
    ( B ) TYPE: amino acid
    ( C ) STRANDEDNESS: single
    ( D ) TOPOLOGY: unknown ( i i ) MOLECULE TYPE: protein ( x i ) SEQUENCE DESCRIPTION: SEQ ID NO: 37:

```
Val Leu Thr Phe His Arg Ile Ile Arg Lys Gly Trp Met Phe Leu Leu
 1               5                  10                  15
Ala Phe Leu Leu Thr Ala Ser Leu Phe Cys Pro Thr Gly Arg His Ala
            20                  25                  30
Lys Ala Ala Ala Pro Phe Asn Gly Thr Met Met Gln Tyr Phe Glu Trp
        35                  40                  45
Tyr Leu Pro Asp Asp Gly Thr Leu Trp Thr Lys Val Ala Asn Glu Ala
    50                  55                  60
Asn Asn Leu Ser Ser Leu Gly Ile Thr Ala Leu Ser Leu Pro Pro Ala
65                  70                  75                  80
Tyr Lys Gly Thr Ser Arg Ser Asp Val Gly Tyr Gly Val Tyr Asp Leu
                85                  90                  95
Tyr Asp Leu Gly Glu Phe Asn Gln Lys Gly Thr Val Arg Thr Lys Tyr
            100                 105                 110
Gly Thr Lys Ala Gln Tyr Leu Gln Ala Ile Gln Ala Ala His Ala Ala
        115                 120                 125
Gly Met Gln Val Tyr Ala Asp Val Val Phe Asp His Lys Gly Gly Ala
    130                 135                 140
Asp Gly Thr Glu Trp Val Asp Ala Val Glu Val Asn Pro Ser Asp Arg
145                 150                 155                 160
Asn Gln Glu Ile Ser Gly Thr Tyr Gln Ile Gln Ala Trp Thr Lys Phe
                165                 170                 175
Asp Phe Pro Gly Arg Gly Asn Thr Tyr Ser Ser Phe Lys Trp Arg Trp
            180                 185                 190
Tyr His Phe Asp Gly Val Asp Trp Asp Glu Ser Arg Lys Leu Ser Arg
    195                 200                 205
Ile Tyr Lys Phe Arg Gly Ile Gly Lys Ala Trp Asp Trp Glu Val Asp
210                 215                 220
Thr Glu Asn Gly Asn Tyr Asp Tyr Leu Met Tyr Ala Asp Leu Asp Met
225                 230                 235                 240
Asp His Pro Glu Val Val Thr Glu Leu Lys Asn Trp Gly Lys Trp Tyr
                245                 250                 255
Val Asn Thr Thr Asn Ile Asp Gly Phe Arg Leu Asp Gly Leu Lys His
            260                 265                 270
Ile Lys Phe Ser Phe Phe Pro Asp Trp Leu Ser Tyr Val Arg Ser Gln
    275                 280                 285
Thr Gly Lys Pro Leu Phe Thr Val Gly Glu Tyr Trp Ser Tyr Asp Ile
290                 295                 300
Asn Lys Leu His Asn Tyr Ile Thr Lys Thr Asn Gly Thr Met Ser Leu
305                 310                 315                 320
Phe Asp Ala Pro Leu His Asn Lys Phe Tyr Thr Ala Ser Lys Ser Gly
                325                 330                 335
Gly Ala Phe Asp Met Arg Thr Leu Met Thr Asn Thr Leu Met Lys Asp
            340                 345                 350
Gln Pro Thr Leu Ala Val Thr Phe Val Asp Asn His Asp Thr Asn Pro
        355                 360                 365
Ala Lys Arg Cys Ser His Gly Arg Pro Trp Phe Lys Pro Leu Ala Tyr
```

|     |     |     |     | 370 |     |     |     |     | 375 |     |     |     |     | 380 |     |
| --- | --- | --- | --- | --- | --- | --- | --- | --- | --- | --- | --- | --- | --- | --- | --- |
| Ala<br>385 | Phe | Ile | Leu | Thr | Arg<br>390 | Gln | Glu | Gly | Tyr | Pro<br>395 | Cys | Val | Phe | Tyr | Gly<br>400 |
| Asp | Tyr | Tyr | Gly | Ile<br>405 | Pro | Gln | Tyr | Asn | Ile<br>410 | Pro | Ser | Leu | Lys | Ser<br>415 | Lys |
| Ile | Asp | Pro | Leu<br>420 | Leu | Ile | Ala | Arg | Arg<br>425 | Asp | Tyr | Ala | Tyr | Gly<br>430 | Thr | Gln |
| His | Asp | Tyr<br>435 | Leu | Asp | His | Ser | Asp<br>440 | Ile | Ile | Gly | Trp | Thr<br>445 | Arg | Glu | Gly |
| Val | Thr<br>450 | Glu | Lys | Pro | Gly | Ser<br>455 | Gly | Leu | Ala | Ala | Leu<br>460 | Ile | Thr | Asp | Gly |
| Ala<br>465 | Gly | Arg | Ser | Lys | Trp<br>470 | Met | Tyr | Val | Gly | Lys<br>475 | Gln | His | Ala | Gly | Lys<br>480 |
| Val | Phe | Tyr | Asp | Leu<br>485 | Thr | Gly | Asn | Arg | Ser<br>490 | Asp | Thr | Val | Thr | Ile<br>495 | Asn |
| Ser | Asp | Gly | Trp<br>500 | Gly | Glu | Phe | Lys | Val<br>505 | Asn | Gly | Gly | Ser | Val<br>510 | Ser | Val |
| Trp | Val | Pro<br>515 | Arg | Lys | Thr | Thr | Val<br>520 | Ser | Thr | Ile | Ala | Arg<br>525 | Pro | Ile | Thr |
| Thr | Arg<br>530 | Pro | Trp | Thr | Gly | Glu<br>535 | Phe | Val | Arg | Trp | His<br>540 | Glu | Pro | Arg | Leu |
| Val<br>545 | Ala | Trp | Pro |  |  |  |  |  |  |  |  |  |  |  |  |

( 2 ) INFORMATION FOR SEQ ID NO: 38:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 38:

| Met<br>1 | Lys | Gln | Gln | Lys<br>5 | Arg | Leu | Thr | Ala | Arg<br>10 | Leu | Leu | Thr | Leu | Leu<br>15 | Phe |
| --- | --- | --- | --- | --- | --- | --- | --- | --- | --- | --- | --- | --- | --- | --- | --- |
| Ala | Leu | Ile | Phe<br>20 | Leu | Leu | Pro | His | Ser<br>25 | Ala | Ala | Ala | Ala<br>30 | Ala | Asn | Leu |

( 2 ) INFORMATION FOR SEQ ID NO: 39:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 39:

| Met<br>1 | Arg | Ser | Lys | Thr<br>5 | Leu | Trp | Ile | Ser | Leu<br>10 | Leu | Phe | Ala | Leu | Thr<br>15 | Leu |
| --- | --- | --- | --- | --- | --- | --- | --- | --- | --- | --- | --- | --- | --- | --- | --- |
| Ile | Phe | Thr | Met<br>20 | Ala | Phe | Ser | Asn | Met<br>25 | Ser | Ala | Gln | Ala | Ala<br>30 | Gly | Lys |
| Ser |  |  |  |  |  |  |  |  |  |  |  |  |  |  |  |

( 2 ) INFORMATION FOR SEQ ID NO: 40:

( i ) SEQUENCE CHARACTERISTICS:
        ( A ) LENGTH: 32 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 40:

```
Met Arg Ser Lys Thr Leu Trp Ile Ser Leu Leu Phe Ala Leu Thr Leu
1               5                   10                  15
Ile Phe Thr Met Ala Phe Ser Asn Met Ser Ala Gln Ala Ala Asn Leu
            20                  25                  30
```